United States Patent [19]
Nair et al.

[11] Patent Number: 5,831,068
[45] Date of Patent: Nov. 3, 1998

[54] METHOD TO INCREASE THE DENSITY OF ANTIGEN ON ANTIGEN PRESENTING CELLS

[75] Inventors: Smita K. Nair; Eli Gilboa, both of Durham, N.C.

[73] Assignee: Duke University, Durham, N.C.

[21] Appl. No.: 700,035

[22] Filed: Aug. 20, 1996

Related U.S. Application Data

[63] Continuation-in-part of Ser. No. 517,373, Aug. 21, 1995, abandoned.

[51] Int. Cl.$^6$ .......................... A61K 45/00; C07H 21/04; C12N 15/85
[52] U.S. Cl. .................... 536/24.5; 424/278.1; 435/325; 435/343.2; 435/375
[58] Field of Search ................................. 536/24.5, 23.1; 435/240.2, 325, 343.2, 375; 424/93.2, 278.1

[56] References Cited

PUBLICATIONS

Kuby J. "Immunology." WH Freeman and Company, NY, pp. 239–249, 1994.

Catherine Sibille et al., "LMP2$^+$ proteasomes are required for the presentation of specific antigens to cytotoxic T Lymphocytes", Current Biology, Aug. 1995, vol. 5, No. 8, pp. 923–930.

Ulrich Steinhoff et al., "Prevention of autoimmune Lysis by T cells with specificity for a heat shock protein by antisense oligonucleotide treatment", Proc. Natl. Acad. Sci., May 1994, vol. 91, No. 5, 5085–5088.

Marja Jaattela et al., "Heat–Shock Proteins Protect Cells from Monocyte Cytotoxicity: Possible Mechanism of Self––Protection", Journal of Experimental Medicine, Jan, 1993, vol. 177, No. 1, pp. 231–236.

*Primary Examiner*—Douglas W. Robinson
*Assistant Examiner*—Amy J. Nelson
*Attorney, Agent, or Firm*—Nixon & Vanderhye P.C.

[57] ABSTRACT

Disclosed is a method for presenting an antigen in the form of a peptide on the surface of a cell. The method involves inhibiting the activity of an MHC class I pathway-associated component (e.g., a TAP protein or a proteasome or its components) in a cell and contacting the cell with an antigenic peptide to produce a potent antigen presenting cell. The antigen presenting cells of the invention can be administered to a mammal in a method of treating or preventing cancer or infection with a pathogen (e.g., a bacterium or virus). If desired, the antigen presenting cells can be used to stimulate CTL proliferation in vitro, and the resulting effector cells can subsequently be administered to a mammal in a method of therapy.

27 Claims, 11 Drawing Sheets

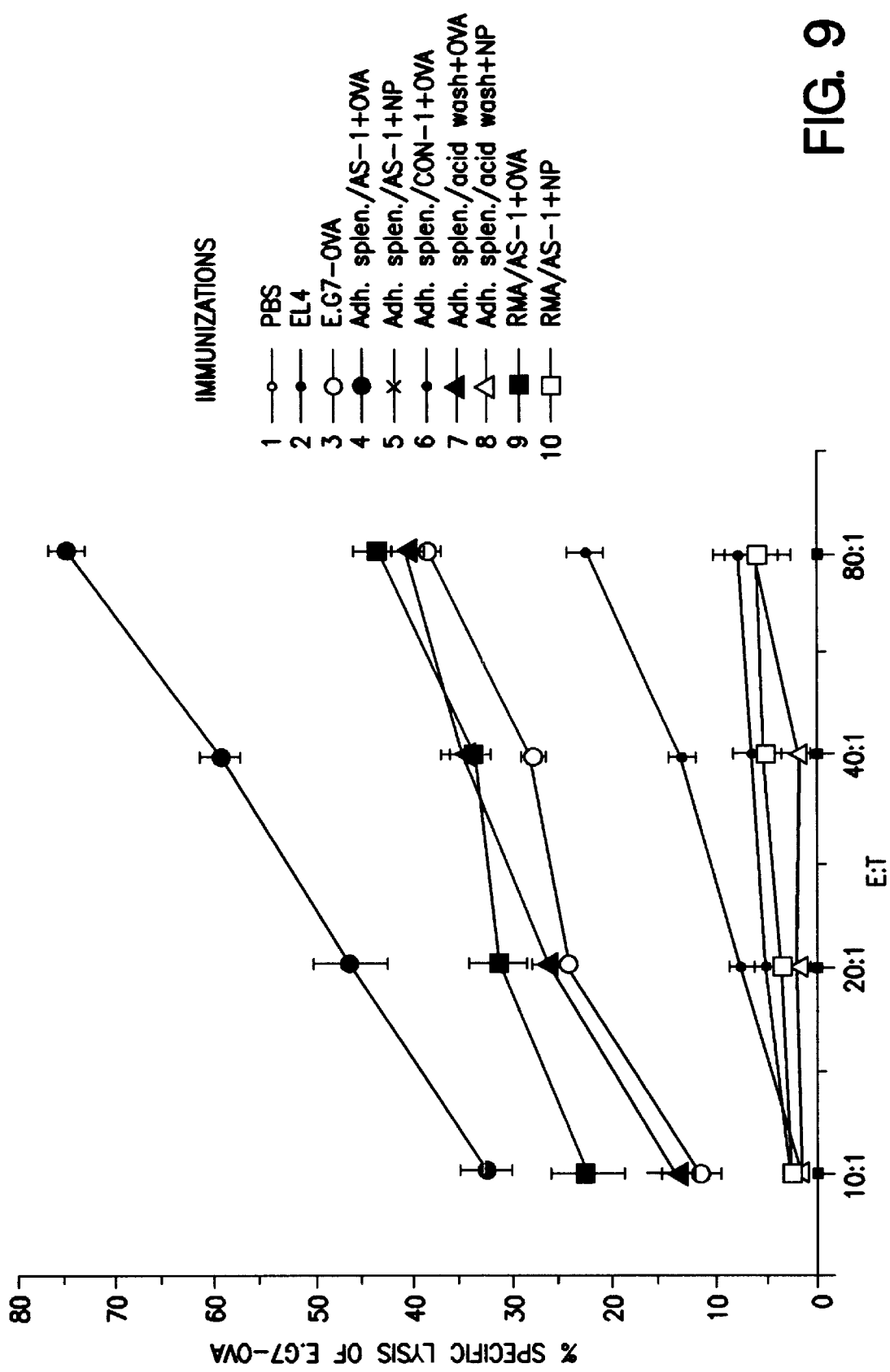

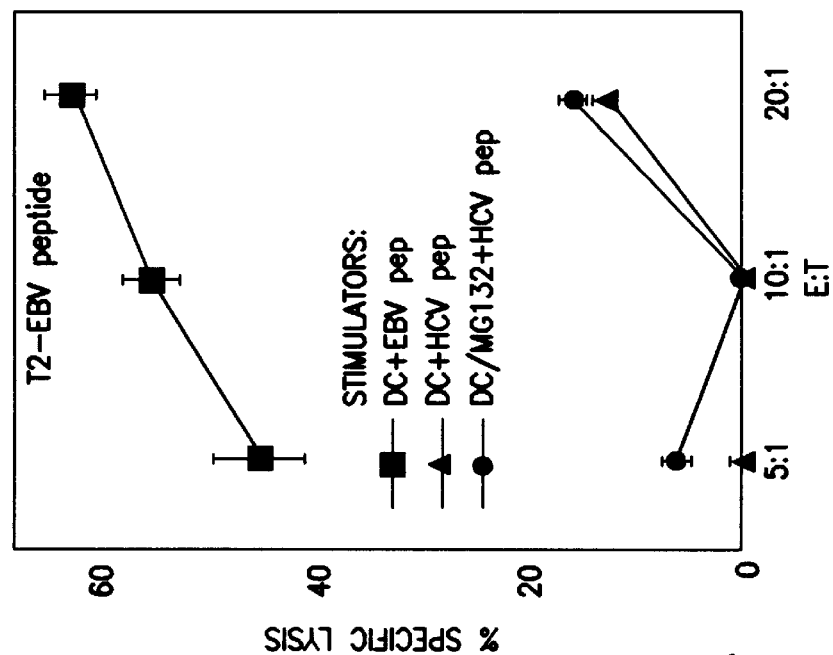
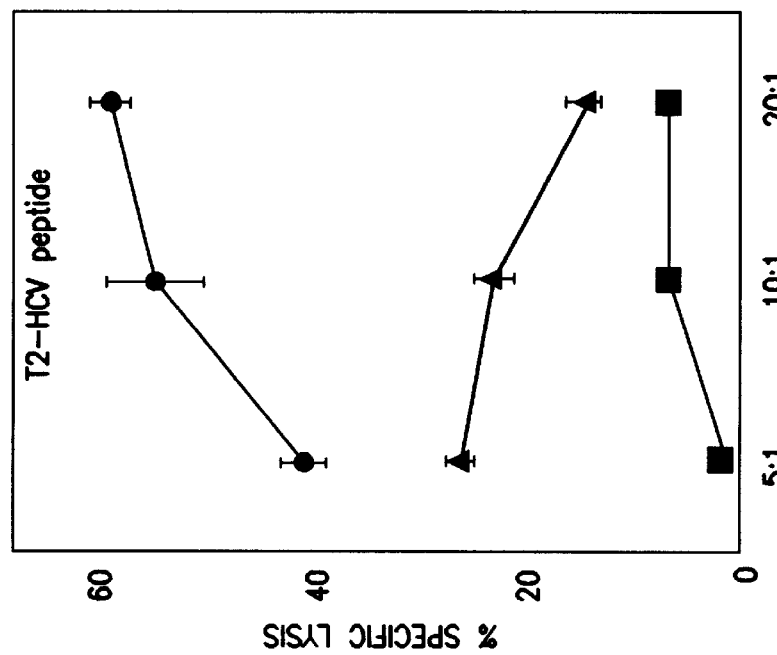

FIG. 11A  FIG. 11B

PRIMARY CTL INDUCTION WITH DC TREATED WITH A PROTEASOME INHIBITOR AND PULSED WITH PEPTIDE

PBMC from HLA-A2 individuals was stimulated with autologous precursor-derived dendritic cells pulsed with EBV or HCV peptide in the presence of B2-microglobulin. Alternatively, DC were treated with the proteasome inhibitor, MG132 (700nm) followed by peptide pulse for 6h. Cytotoxicity was measured against peptide pulsed T2 cells. PBMC were stimulated on day 0 and day 14 with peptide-pulsed DC and IL-7 and IL-2. CTL assay was done on day 20.

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 25 base pairs
        ( B ) TYPE: nucleic acid ( C ) STRANDEDNESS: single
        ( D ) TOPOLOGY: linear ( x i ) SEQUENCE DESCRIPTION: SEQ ID NO:1:

AGGGCCTCAG GTAGGACAGC GCCAT 25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCAGCAGGAT ATTGGCATTG AAAGG 25

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGAGAAGCTC AGCCATTTAG GG 22

( 2 ) INFORMATION FOR SEQ ID NO:4:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

CACAGCCTCC TTCTGGTTGA GTGTCTT 27

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ATCATCCAGG ATAAGTACAC ACGGTTT 27

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TCTCAGGTCA GGGAGCGGCA TGG 23

( 2 ) INFORMATION FOR SEQ ID NO:7:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTCTACATCG CTCCAGGGCC TCCTT 25

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

ACGAAAAGGA GACGTCTTGG AATTC 25

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TACCGCGACA GGATGGACTC CGGGA 25

( 2 ) INFORMATION FOR SEQ ID NO:10:

( i ) SEQUENCE CHARACTERISTICS:
        ( A ) LENGTH: 4 amino acids
        ( B ) TYPE: amino acid
        ( C ) STRANDEDNESS: Not Relevant
        ( D ) TOPOLOGY: linear ( i i ) MOLECULE TYPE: protein ( x i ) SEQUENCE DESCRIPTION: SEQ ID NO:10:

Leu Leu Val Tyr
1

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:11:

Ser Ile Ile Asn Phe Glu Lys Leu
1               5

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:12:

Ser Asp Tyr Glu Gly Arg Leu Ile
1               5

(2) INFORMATION FOR SEQ ID NO:13:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:13:

```
Thr  Tyr  Gln  Arg  Thr  Arg  Ala  Leu  Val
 1                    5
```

(2) INFORMATION FOR SEQ ID NO:14:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:14:

```
Ala  Ser  Asn  Glu  Asn  Met  Glu  Thr  Met
 1                    5
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:15:

```
Cys  Ile  Asn  Gly  Val  Cys  Trp  Thr  Val
 1                    5
```

(2) INFORMATION FOR SEQ ID NO:16:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:16:

```
Cys  Leu  Gly  Gly  Leu  Leu  Thr  Met  Val
 1                    5
```

METHOD TO INCREASE THE DENSITY OF ANTIGEN ON ANTIGEN PRESENTING CELLS

CROSS-REFERENCE TO RELATED APPLICATION

This application is a continuation-in-part of U.S. application Ser. No. 08/517,373, filed Aug. 21, 1995 now abandoned.

BACKGROUND OF THE INVENTION

This invention relates to presentation of antigen on a cell.

Cytotoxic CD8+T lymphocytes (CTL) recognize peptides derived from endogenously processed viral, bacterial, or cellular proteins, in association with major histocompatibility complex (MHC) class I molecules (Zinkernagel et al., Advanced Immunol. 27:51–180, 1979). CTL epitopes, consisting of 8–10 amino acid long peptides, are generated from endogenously synthesized proteins in the cytosol, enter the endoplasmic reticulum where they associate with newly synthesized MHC class I molecules, and are then translocated to the cell surface for presentation to CD8+T cells (Townsend et al., Annu. Rev. Immunol. 7:601–624, 1989; Monaco, Cell 54:777–785, 1992; Yewdell et al., Adv. in Immunol. 52:1–123, 1992).

Genetic analysis has played an important role in elucidating the pathway of MHC class 1-restricted antigen processing and presentation. Studies of antigen presentation-defective human and murine cell lines have demonstrated the requirement of transporter associated with antigen processing (TAP) proteins to transport peptides into the endoplasmic reticulum, where their association with MHC class I molecules is a prerequisite for class I assembly (Townsend et al., Eur. J. Immunogenetics 19:45–55, 1993). Mutagenesis of RMA cells, a cell line derived from the Rauscher virus induced lymphoma of C57BL/6 (H-$2^b$) origin, and selection for loss of MHC class I expression led to the isolation of the mutant cell line RMA-S, which expresses cell surface MHC class I molecules at reduced levels. This cell line, which is deficient in expressing the TAP protein TAP-2, is unable to present endogenously processed MHC class I restricted antigens to CD8+ T cells (Ljunggren et al., J. Exp. Med. 162:1745–1759, 1985; Kärre et al., Nature 319:675–678, 1986; Öhlén et al., J. Immunol. 145:52–58, 1990; and Cerundolo et al., Nature 345:449–456, 1990).

The presentation of antigen via the MHC class I pathway is mediated by several MHC class I pathway-associated proteins in addition to the TAP proteins. For example, the low molecular weight proteins LMP 2 and LMP 7 serve as subunits of the proteasome, a multicatalytic proteinase complex that is thought to degrade cellular proteins in order to generate the peptides that associate with MHC class I molecules. Once generated, the peptides associate with heat shock proteins (HSP; e.g., gp 96, HSP 90, and HSP 70), which act as chaperones to help transport the peptides from proteasomes to the nascent MHC molecules.

SUMMARY OF THE INVENTION

Applicants have discovered that an antigen in the form of an MHC-binding peptide epitope can be presented on a cell by inhibiting activity of an MHC class I pathway-associated component (e.g., a TAP protein or a proteasome) in the cell prior to contacting the cell with the antigen. The cells produced according to this method are potent antigen presenting cells useful for stimulating an immune response in vitro or in vivo.

Accordingly, in one aspect, the invention features a method for altering the presentation of an antigen (e.g., antigen in the form of a peptide) that is contacted with a cell; the method entails inhibiting activity of an MHC class I pathway-associated component in the cell prior to contacting the cell with the antigen (e.g., peptide). Inhibiting the activity of an MHC class I pathway-associated component can be accomplished by inhibiting expression of an MHC pathway-associated protein or by contacting the cell with a compound (i.e., an inhibitor) that inhibits the ability of an MHC pathway-associated component to perform a natural biological function. If desired, inhibiting expression of the MHC pathway-associated component can readily be accomplished by inhibiting translation of an MHC class I pathway-associated protein. For example, translation can be inhibited by introducing into a cell an antisense (AS) oligonucleotide that is complementary to all or a portion of a mRNA encoding the MHC class I pathway-associated protein or by expressing in the cell an antisense gene that encodes an RNA that is complementary to all or a portion of a mRNA encoding a MHC class I pathway-associated protein. In another embodiment of the invention, inhibiting the activity of an MHC pathway-associated protein involves introducing into the cell a decoy RNA that binds to an MHC class I pathway-associated protein and inhibits the function of the protein.

In yet another embodiment of the invention, inhibition is accomplished by introducing into the cell a ribozyme that specifically cleaves an mRNA encoding an MHC class I pathway-associated protein, thereby inhibiting translation of the MHC class I pathway-associated protein. In still another method, the activity of an MHC pathway-associated component is inhibited by contacting the cell with a proteasome inhibitor, such as LLnL, MG115, MG132, CEP690, CEP1508, CEP1612, CEP1513, or lactacystin. All of these inhibitors are known in the art (see, e.g., Hughes et al., 1996, J. Exp. Med. 183:1569–1576; Rock et al., 1994, Cell 78:761–771; Yang et al., 1996, J. Exp. Med. 183:1545–1552; Harding et al., 1995, J. Immunol. 22:1767–1775; and Fenteany et al., Science 268: 726–731). Additional compounds can readily be identified as proteasome inhibitors by comparing the activity of putative inhibitors with the activity of known proteasome inhibitors.

Inhibiting the function of one or more components of the class I antigen processing pathway results in cells deficient in endogenous peptide loading. Contacting the cell with an exogenous antigenic peptide results in loading of empty class I molecules and is an efficient method for producing an antigen-presenting cell having an increased density of antigen (relative to the density of antigen obtained by employing the natural MHC class I antigen presentation pathway).

Preferably, the MHC class I pathway-associated component is a protein, such as a TAP protein (e.g., TAP-1 or TAP-2). Other preferred MHC class I pathway-associated proteins include, but are not limited to, LMP 2, LMP 7, gp 96, HSP 90, and HSP 70. If desired, AS oligonucleotides, AS genes, decoy RNAs, proteasome inhibitors, and/or ribozymes can be used to inhibit expression of a combination of MHC class I pathway-associated components (e.g., TAP-1 and LMP 7). Genes encoding MHC class I pathway-associated proteins have been cloned and sequenced (see, e.g., Trowsdale et al., 1990, Nature 348: 741–748, GenBank Accession No. X57522; Bahram et al., 1991, Proc. Natl. Acad. Sci. 88:10094–10098, GenBank Accession No. M74447; Monaco et al., 1990, Science 250: 1723–1726, GenBank Accession No. M55637; and Yang et al., 1992, J. Biol. Chem. 267:11669–11672, Gensank Accession No. M90459).

Examples of preferred antisense oligonucleotides directed against murine TAP-2 include oligonucleotides having the following sequences:

5'AGGGCCTCAGGTAGGACAGCGCCAT3' (SEQ ID NO: 1) and

5'GCAGCAGGATATTGGCATTGAAAGG3' (SEQ ID NO: 2).

Examples of preferred antisense oligonucleotides directed against human TAP-1 include oligonucleotides having the following sequences:

5'CGAGAAGCTCAGCCATTTAGGG3' (SEQ ID NO: 3),

5'CACAGCCTCCTTCTGGTTGAGTGTCTT3' (SEQ ID NO: 4), and 5'ATCATCCAGGATAAGTACACACG-GTTT3' (SEQ ID NO: 5).

These AS oligonucleotides are complementary to nucleotides 46–25, 1428–1402, and 2214–2188 of human TAP-1. A preferred antisense oligonucleotide directed against human TAP-2 is complementary to nucleotides 117–92 and has the sequence 5'TCTCAGGTCAGGGAGCGGCATGG3' (SEQ ID NO: 6). Portions of these oligonucleotides, or longer oligonucleotides that include these sequences, can also be used in the invention.

Any antigenic peptide that is naturally presented on the surface of an antigen-presenting cell can be employed in the invention. Preferably, the antigen is a polypeptide that includes a portion of a protein naturally expressed by a pathogen, such as a bacterium or a virus. If desired, the antigen can be a tumor-specific antigen (i.e., an antigen that is preferentially expressed or present in a tumor cell compared with a non-tumor cell). An antigen presenting cell produced with a tumor-specific antigen can be administered to a mammal in a method of treating or preventing cancer (e.g., a malignant tumor, a carcinoma, or a sarcoma).

Also within the invention is a cell produced by any of the methods described herein. Such a cell can contain an antisense oligonucleotide that reduces expression of an MHC class I pathway-associated protein (e.g., a TAP protein). In addition, or in the alternative, a cell of the invention can contain an antisense gene that encodes an RNA (i.e., an antisense RNA) that is complementary to all or a portion of an mRNA encoding an MHC class I pathway-associated protein and which antisense RNA inhibits translation of the mRNA. Also included within the invention is a cell that contains a decoy RNA that binds to an MHC class I pathway-associated protein and inhibits the function of the protein. In addition, the invention includes a cell that contains a ribozyme that specifically cleaves an mRNA encoding an MHC class I pathway-associated protein, and which thereby inhibits translation of the MHC class I pathway-associated protein. The invention also includes an antigen presenting cell produced by contacting a cell with a proteasome inhibitor and an antigenic peptide.

A variety of cells can be used in the invention. Preferably, the cell is a mammalian cell, such as a human or mouse cell. The cell can be a primary cell, or it can be a cell of an established cell line. Preferably, the cell is one of the following: a T lymphocyte (e.g., a RMA cell), a B lymphocyte, an adherent or non-adherent splenocyte, an adherent or non-adherent peripheral blood mononuclear cell (PBMC), a dendritic cell (e.g., a spleen-derived dendritic cell, a Langerhans'-dendritic cell, a follicular dendritic cell, or a precursor-derived dendritic cell), a macrophage, a thymoma cell (e.g., an EL4 cell), or a fibroblast. If desired, a combination of cells can be used in the invention. For example, the activity of an MHC class I pathway-associated component can be inhibited in a mixture of adherent and non-adherent PBMC.

The cell(s) of the invention can be administered to a mammal, e.g., in a method of treating or preventing a pathogen (e.g., a bacterium or virus) infection or a cancer in a mammal. Such a cell(s), when combined with a pharmaceutically acceptable excipient, provides a vaccine against a protein (e.g., a toxin of a bacterium) containing the antigen with which the cell was contacted. Accordingly, such a vaccine can be used in treating or preventing cancer or a pathogen infection (e.g., an intracellular pathogen infection).

In one embodiment, a cell of the invention is allowed to contact a T lymphocyte in a method for stimulating cytotoxic T lymphocyte (CTL) proliferation in vitro. The invention thus includes a CTL produced by inhibiting activity of an MHC class I pathway-associated component (e.g., a TAP protein or proteasome) in a cell, contacting the cell with an antigen, thereby producing an antigen presenting cell, and contacting a T lymphocyte with the antigen presenting cell in vitro, thereby producing a cytotoxic T lymphocyte. Such a CTL can be administered to a mammal in a method of therapy (e.g., for treating or preventing infection with a pathogen, or for treating or preventing cancer, e.g., a malignant tumor).

By MHC class I "pathway-associated" component is meant any of the components (e.g., proteins or protein complexes) that function to process or present an antigen on the surface of the cell in association with an MHC class I molecule. Examples of MHC class I pathway-associated components include 26S proteasomes and 20S proteasomes; components of proteasomes, such as LMP proteins (e.g., LMP 2 and LMP 7) also are included. In addition, the term MHC class I pathway-associated component includes various MHC class I pathway-associated proteins, such as TAP proteins (e.g., TAP-1 and TAP-2) and heat shock proteins (e.g., gp 96, HSP 70, and HSP 90).

By "TAP protein" is meant any of the ATP-binding MHC-encoded polypeptides that translocates antigenic peptides, as described by Momburg et al., for example (Momburg et al., 1994, Curr. Opin. Immunol. 6:32–37). Preferably, the gene encoding the TAP protein has at least 80%, more preferably 90%, and most preferably 100%, sequence identity to the previously reported human or murine TAP-1 or TAP-2 genes (see, e.g., Trowsdale, Bahram, Monaco, and Yang et al., supra).

By "decoy" RNA is meant an RNA molecule that specifically binds an MHC class I pathway-associated protein and inhibits or prevents the protein from interacting with its normal cellular counterpart(s), thereby decreasing MHC class I cell surface expression. Such decoy RNA molecules can be isolated and identified with the previously described Selex selection procedure, for example (see, e.g., Doudna et al., 1995, Proc. Natl. Acad. Sci. 92: 2355–2359).

The invention offers several advantages. For example, if desired, inhibiting the activity of an MHC class I pathway-associated component can be accomplished in a rapid and transient manner by employing antisense oligonucleotides or proteasome inhibitors. The use of proteasome inhibitors is a particularly convenient method for producing antigen presenting cells having an increased density of antigen. Where long-term inhibition of protein expression is desired, an antisense gene is particularly suitable for use in the invention. The invention also provides a means for manipulating antigen presentation in cells of any haplotype. In addition, the invention can make use of primary cells; such cells, obtained from a patient or donor can be manipulated in vitro using the methods of the invention, and then be administered to a patient.

Other features and advantages of the invention will be apparent from the following description of the preferred embodiments, and from the claims.

The following abbreviations are used herein.

| APC | antigen-presenting cell |
|---|---|
| AS | antisense |
| BSA | bovine serum albumin |
| CTL | cytotoxic T lymphocyte |
| FACS | fluorescence-activated cell sorting |
| FCS | fetal calf serum |
| FITC | fluorescein isothiocyanate |
| LMP | low molecular weight protein |
| NP | nucleoprotein |
| nt | nucleotide |
| OVA | ovalbumin |
| PBMC | peripheral blood mononuclear cell(s) |
| TAP | transporter associated with antigen processing |

BRIEF DESCRIPTION OF THE DRAWINGS

FIG. 1A is a graph obtained with an isotypic control antibody. FIG. 1B is a graph representing untreated RMA cells. FIG. 1C is a graph representing RMA cells treated with AS-1. FIG. 1D is a graph representing RMA cells treated with AS-2. FIG. 1E is a graph representing RMA cells treated with AS-3. FIG. 1F is a graph obtained with RMA cells treated with AS-4.

FIG. 2A is a graph representing MHC class I expression on RMA-S cells incubated at 37° C. FIG. 2B is a graphic representation of MHC class I RMA-S cells incubated at 28° C. FIG. 2C is a graph obtained with untreated RMA cells incubated at 37° C. FIG. 2D is a graph obtained with untreated RMA cells incubated at 28° C. FIG. 2E is a graph representing RMA cells treated with AS-1 at 37° C. FIG. 2F is a graph representing in AS-1 treated RMA cells incubated at 28° C.

FIG. 3A is a graph representing CON-1 treated RMA cells. FIG. 3B is a graph representing AS-1 treated RMA cells. FIG. 3C is a graph representing AS-1 treated RMA cells incubated with the haplotype mis-matched peptide NP (H-2K$^d$). FIG. 3D is a graph representing AS-1 treated RMA cells incubated with the haplotype mis-matched peptide NP (H-2K$^k$). FIG. 3E is a graph representing AS-1 treated RMA cells incubated with the haplotype matched peptide NP (H-2D$^b$). FIG. 3F is a graph representing the haplotype matched peptide OVA (H-2K$^b$).

FIG. 4A is a graph obtained with untreated EL4 cells. FIG. 4B is a graph obtained with CON-1 treated EL4 cells. FIG. 4C is a graph obtained with AS-1 treated EL4 cells. FIG. 4D is a graph obtained with AS-1 treated EL4 cells incubated at 28° C. FIG. 4E is a graph obtained with AS-1 treated EL4 cells incubated with the haplotype matched peptide OVA (H-2K$^b$). FIG. 4F is a graph obtained with AS-1 treated EL4 cells incubated with the haplotype mis-matched peptide NP (H-2K$^k$).

FIGS. 5A and 5B are graphs obtained with untreated, unfractionated splenocytes incubated at 37° C. and 28° C., respectively. FIGS. 5C and 5D are graphs obtained with AS-1 treated unfractionated splenocytes incubated at 37° C. and 28° C., respectively. FIGS. 5E and 5F are graphs obtained with AS-1 treated adherent cells incubated at 37° C. and 28° C., respectively. FIGS. 5G and 5H are graphs obtained with AS-1 treated non-adherent cells incubated at 37° C. and 28° C., respectively.

FIG. 8A is a histogram representing CTL responses at a responder:stimulator ratio of 4:1. FIG. 8B is a histogram representing CTL responses at a responder:stimulator ratio of 8:1.

FIG. 9 is a graphic representation of CTL responses obtained in vivo with mice inoculated with PBS (line 1), EL4 cells (line 2), E.G7 cells transfected with the OVA gene (line 3), AS-1 treated adherent splenocytes incubated with a haplotype matched OVA peptide (line 4), AS-1 treated adherent splenocytes incubated with a haplotype mis-matched NP peptide (line 5), CON-1 treated adherent splenocytes incubated with a haplotype matched OVA peptide (line 6), acid-treated adherent splenocytes incubated with a haplotype matched OVA peptide (line 7), acid-treated adherent splenocytes incubated with a haplotype mis-matched NP peptide (line 8), AS-1 treated RMA cells incubated with a haplotype matched OVA peptide (line 9), or AS-1 treated RMA cells incubated with a haplotype mis-matched NP peptide (line 10).

FIGS. 11A–11B are a pair of graphs schematically representing the induction of primary CTL using dendritic cells that were treated with a proteasome inhibitor and pulsed with peptide. The graphs represent the cytotoxicity of CTL that were produced by using as stimulators dendritic cells that had been treated with a proteasome inhibitor and pulsed with antigenic peptide. The CTL targets were T2 cells that had been pulsed with HCV peptide (FIG. 11A) or EBV peptide (FIG. 11B). The CTL assays were performed at the indicated effector:target (E:T) ratios.

DETAILED DESCRIPTION OF THE INVENTION

Figure 1A:
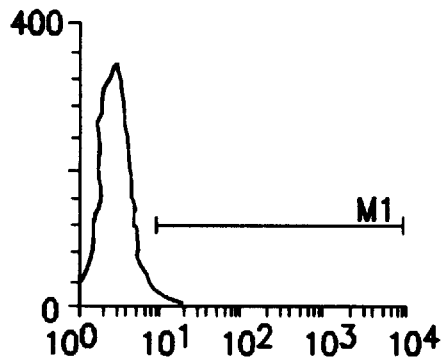
FIGS. 1A–1F are a series of FACS-generated graphs representing MHC class I expression in RMA cells treated with TAP-2 AS oligonucleotides.

Antisense Oligonucleotides: The oligonucleotides that are useful in the invention can be prepared with conventional methods for synthesizing DNA. Generally, the AS oligonucleotides to be used in the invention are those that destabilize the mRNA of an MHC class I pathway-associated protein. AS oligonucleotides that are complementary to the region spanning the initiation codon (i.e., all or a portion of nucleotides 1 to 25 of the coding sequence) generally are suitable destabilizers. Preferably, the AS oligonucleotide is complementary to a region of the mRNA which, based on conventional methods for predicting secondary structure, is not expected to form a complex secondary structure. In the experiments described herein, the MULFOLD computer program (Jaeger et al., 1989, Proc. Natl. Acad. Sci. 86:7706–7710) was utilized to characterize the secondary structure of the TAP-2 mRNA.

As an alternative to predicting preferred antisense oligonucleotides, one may readily test an arbitrarily selected oligonucleotide. Examples of preferred AS oligonucleotides are provided in Table 1. Preferably, the AS oligonucleotide is 15 to 40 nucleotides in length; more preferably, the oligonucleotide is 20 to 30 (e.g., 25) nucleotides in length. Generally, an oligonucleotide having a GC content of 50 to 60%, and having no more than 3 consecutive guanines is preferable in order to inhibit secondary structure formation yet allow the formation of stable hybrids between the AS oligonucleotide and the TAP mRNA.

to nucleotides 815–790 of TAP-2 and has the sequence: 5'GCAGCAGGATATTGGCATTGAAAGG3' (SEQ ID NO: 2). AS-3 is complementary to nucleotides 1,088 to 1,063 of TAP-2 and has the sequence: 5'GTCTACATCGCTCCA GGGCCTCCTT3' (SEQ ID NO: 7). AS-4 is complementary to nucleotides 1,427–1,402 and has the sequence: 5'ACGAAAAGGA GACGTCTTGGAATTC3' (SEQ ID NO: 8). The following working examples employed, as a control, the oligonucleotide CON-1, which is identical to nucleotides 1–25 of TAP-2 mRNA. With the sequence 5'TACCGCGACAGGATGGACTCCGGGA3' (SEQ ID NO: 9), CON-1 has the same nucleotide content as AS-1.

Antisense Genetic Constructs: Expression of a gene encoding an MHC class I pathway-associated protein in a cell can also be inhibited by introducing an antisense genetic construct (e.g., plasmid) into the cell. Such an antisense genetic construct includes all or a portion of a gene encoding an MHC class I pathway-associated protein (e.g., TAP-1) (the antisense gene) operably linked to a promoter, and positioned such that expression of the gene produces a transcript that is complementary to all or a portion of a naturally-occurring mRNA of an MHC class I pathway-associated protein. In practice, such an antisense gene is positioned adjacent the promoter in the "reverse" orientation, relative to the naturally-occurring gene encoding an MHC class I pathway-associated protein. Where the antisense gene produces a transcript that is complementary to a portion of the mRNA, particularly useful transcripts are those that include all or a portion of the sequences that can be used as AS oligonucleotides (e.g., sequences listed in Table 1).

A variety of vectors are suitable for constructing antisense genetic constructs. Preferably, the vector is a retroviral vector that has a strong promoter for efficient expression in a mammalian cell (e.g., an N2 vector (Armentano et al., 1987, J. Virol. 61:1647–1650)). If desired, the promoter that drives expression of the antisense gene may be a cell- or tissue-specific promoter. Such a retroviral vector encoding the antisense gene can be delivered to the cell in a lipid-mediated transfection method (e.g., using 5–20 μg DNA and 20–50 μg lipid). If desired, the genetic construct may be

TABLE 1

| AS OLIGONUCLEOTIDE | SEQ ID NO | COMPLEMENTARY SEQ. |
|---|---|---|
| 5'AGGGCCTCAGGTAGGACAGCGCCAT3' | 1 | mTAP-2 nt 1-25 |
| 5'GCAGCAGGATATTGGCATTGAAAGG3' | 2 | mTAP-2 nt 815-790 |
| 5'CGAGAAGCTCAGCCATTTAGGG3' | 3 | hTAP-1 nt 46-25 |
| 5'CACAGCCTCCTTCTGGTTGAGTGTCTT3' | 4 | hTAP-1 nt 1428-1402 |
| 5'ATCATCCAGGATAAGTACACACGGTTT3' | 5 | hTAP-1 nt 2214-2188 |
| 5'TCTCAGGTCAGGGAGCGGCATGG3' | 6 | hTAP-2 nt 117-95 |

If desired, the AS oligonucleotide can be synthesized with modified nucleotides (e.g., to increase the in vivo half-life of the AS oligonucleotide). For example, modified nucleotides, such as phosphorothioate derivatives, may be used. For convenience, AS oligonucleotides prepared by a commercial supplier (e.g., Oligos Etc., Wilsonville, Oreg.) may be used in the invention. Oligonucleotides that are to be added to cells in culture can conveniently be stored at −20° C. as a sterile, 100 μM solution in serum-free medium.

The four AS oligonucleotides employed in the working examples summarized below (AS-1, AS-2, AS-3, and AS-4) were synthesized as phosphorothioate derivatives. AS-1 is complementary to nucleotides 1–25 of the murine TAP-2 mRNA and has the sequence: 5'AGGGCCTCAGGTAGGA-CAGCGCCAT3' (SEQ ID NO: 1). AS-2 is complementary designed to contain sequences for recombination such that all or a portion of the genetic construct is incorporated into the genome of the mammal in which expression an MHC class I pathway-associated protein is to be inhibited. Incorporation of the antisense gene into the mammalian cell genome offers the advantage that the antisense gene is stably expressed in the cell, diminishing the need for repeated administration of the antisense nucleic acid. Stable incorporation of the antisense gene is particularly desirable where the invention is employed to present an antigen on a hematopoietic stem cell (e.g., for expressing HIV antigens in hematopoietic cells in a method of treating HIV infection). Various methods for expressing a gene in a cell in a method of therapy are known and can readily be adapted for expressing an antisense gene in practicing the invention (see, e.g., U.S. Pat. No. 5,399,346, incorporated herein by reference).

Introduction of an Antisense Oligonucleotide Into a Cell: Art-known methods may be used to introduce an AS oligonucleotide into a cell. For example, a non-toxic cationic lipid (e.g., LIPOFECTIN™ (1:1 (w/w) DOTMA:DOPE)) may be used to deliver the AS oligonucleotide or gene to the cell. In the working examples set forth below, tumor cells (in log phase) or splenocytes were first washed twice in Opti-MEM medium (GIBCO, Grand Island, N.Y.). Other culture media that support cell growth could substitute for Opti-MEM. The cells then were resuspended in Opti-MEM medium to a concentration of $5-10\times10^6$ cells/ml, and the cells were added to 24-well or 6-well plates. LIPOFECTIN™ (1:1 (w/w) DOTMA:DOPE) was used to deliver oligonucleotides into cells according to the method of Chiang et al. (1991, J. Biol. Chem. 266:18162–18171). The oligonucleotide and LIPOFECTIN ™ (1:1 (w/w) DOTMA:DOPE) were added to Opti-MEM medium at the desired concentration and mixed in a 12×75 mm polystyrene tube at room temperature for 20 minutes. The resulting oligonucleotide-cationic lipid complex was added to the cells to achieve a final concentration of 400 nM oligonucleotide and 15 µg/ml LIPOFECTIN™ (1:1 (w/w) DOTMA:DOPE), and the cells were incubated at 37° C. for 6–8 hours. Generally, an oligonucleotide concentration of 200–800, preferably 200–500 nM is suitable. A cationic lipid concentration of 10–40 µg/ml is generally appropriate. If desired, the DNA and cationic lipid complex may be incubated with the cell for longer than 6 hours (e.g., up to 24 or 48 hours) to facilitate formation of the complex.

In the below examples, the cells were washed following incubation, and then incubated at 28° C. or 37° C. for 24–48 hours. The cells then were assayed by flow cytometry for MHC class I expression; alternatively, the cells were used as stimulators for induction of a CTL response. If desired, other, non-lipid-based methods may be used to introduce the AS oligonucleotide or gene into cells. For example, electroporation is appropriate; alternatively, incubating the cell with a high concentration (e.g., 4–30 µM) of oligonucleotide is also useful for introducing an AS oligonucleotide into a cell. Of course, a combination of these methods also can be used.

Ribozymes: Inhibition of expression of an MHC class I pathway-associated protein in a cell can also be accomplished by introducing into the cell a ribozyme that is designed to cleave an mRNA encoding an MHC class I pathway-associated protein. For example, a hammerhead ribozyme can be constructed according to conventional procedures such that the arms flanking the hammerhead of the ribozyme are complementary to a portion of the mRNA encoding the MHC class I pathway-associated protein. Expression of the ribozyme, e.g., from a retroviral vector, leads to RNA catalysis and cleavage of the targeted RNA sequence (see, e.g., Sullenger and Cech, 1993, Science 262:1566–1569). Preferably, the flanking arms are 15–25 nucleotides in length. If desired, the ribozyme can be designed to include a hammerhead ribozyme having flanking arms that include sequences corresponding to the preferred AS oligonucleotides. Generally, it is preferred that the flanking arms are complementary to the 5' most region of the mRNA encoding the MHC class I pathway-associated protein.

Decoy RNAs: A decoy RNA can be used to inhibit expression (i.e., the function) of an MHC class I pathway-associated protein in a cell. Methods for identifying decoy RNAs for proteins that do not normally bind RNAs have been described (see, e.g., Doudna et al., 1995, Proc. Natl. Acad. Sci. 2355–2359). Briefly, decoy RNAs are first selected on the basis of their ability to bind the targeted MHC class I pathway-associated protein. In this method, a pool of RNA oligonucleotides having approximately 40 random nucleotides (with equimolar A, G, C, and U at each position) flanked by pre-selected sequences is incubated with the targeted MHC class I pathway-associated protein (e.g., TAP-1). RNAs that bind the MHC class I pathway-associated protein are isolated (e.g., by immunoprecipitation of the protein/RNA complex) and amplified (e.g., using primers complementary to the pre-selected flanking sequences for cDNA synthesis and transcription). Preferably, subsequent cycles (e.g., 10 cycles) of selection are performed with the resulting RNA. Because the initial pool of RNA molecules includes sequences that are completely random, all possible decoy RNAs are screened with this method. Decoy RNAs selected with this method can be introduced into a cell (e.g., by expressing the RNA from a retroviral vector), and cell surface expression of MHC class I molecules can be measured as described herein.

Proteasome Inhibitors: A variety of proteasome inhibitors are known in the art and can be used in the invention. Preferred inhibitors are those compounds that have been identified as inhibiting (or preventing) the ability of a 20S or 26S proteasome to degrade proteins that normally are degraded during the process of presenting peptides on MHC molecules (see Rock et al., 1994, Cell 78:781–771; Orino et al., 1991; Goldberg et al., 1992; Hershko and Ciechanover, 1992; Rechsteiner et al., 1993). Preferably, the proteasome inhibitor is a competitive inhibitor of the hydrolysis of Suc-Leu-Leu-Val-Tyr-AMC (SEQ ID NO: 10) (see Rock et al., 1994, Cell 78:761–771).

Examples of preferred inhibitors include the peptide aldehydes

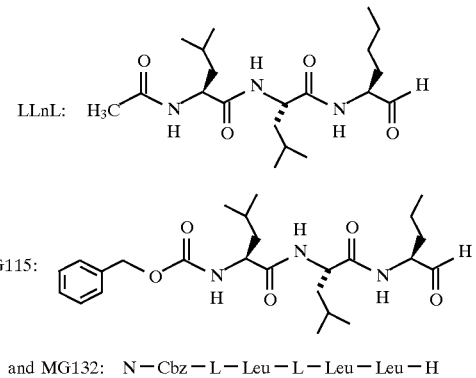

and MG132: N—Cbz—L—Leu—L—Leu—Leu—H

Other preferred proteasome inhibitors include:

lactacystin:

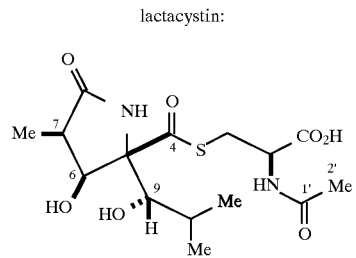

CEP690, CEP1508, CEP1612, CEP1513, and CEP1612:

-continued

| Compound | R | n | W | X | Z |
|---|---|---|---|---|---|
| 1508 | NC— | 8 | cyclopentyl | NO$_2$ | O |
| 1601 | NC— | 8 | cyclopentyl | NO$_2$ | NNHCONH$_2$ |
| 1513 | MeOOC— | 7 | cyclopentyl | PMC | O |
| 1612 | C$_6$H$_4$(CO)$_2$N | 8 | cyclopentyl | NO$_2$ | O |
| 690 | MeOOC— | 6 | H | MTR | O |

(PMC = 2,2,5,7,8-pentamethylchroman-6-sulfonyl. MTR = 4-methoxy-2,3,6-trimethylbenzene-1-sulfonyl)
Structure of dipeptide aldehyde proteasome inhibitors. The PMC and MTR groups are covalently linked to the nitrogen at position X via the sulfur in each compound (i.e., a sulfonyl linkage).
Also included is CEP1601.

Where a proteasome inhibitor is used in the invention, the inhibitor typically is contacted with a cell at a concentration of 1.0 μM to 50 μM. MG132 is a particularly potent inhibitor, and thus can be used at concentrations as low as 100 nM to 1,000 nM, preferably 500 nM to 800 nM. The proteasome inhibitors used in the invention are allowed to remain in contact with the cell for 30 to 120 minutes before the cell is contacted with antigenic peptide as described herein. Optionally, the cell can be washed (e.g., with cell culture media) prior to contacting the cell with antigenic peptide.

Cell Lines: The invention can be used to present antigen on a variety of cell types derived from humans or other mammals (e.g., mice). Generally, cells on which MHC class I molecules or HLA determinants are expressed at relatively high levels (e.g., macrophages) are preferred to cells on which MHC molecules or HLA determinants are expressed at relatively low levels. The cell can be a primary cell, or it may be a cell of an established cell line. Generally, cells that are actively endocytic are expected to take up the AS oligonucleotide or AS gene more efficiently than do less endocytic cells. Particularly useful cells include primary macrophages, immature dendritic cells, and cells of macrophage derived-cell lines. The RMA and RMA-S cells used in the working examples set forth below are derived from the Rauscher leukemia virus-induced T cell lymphoma RBL-5 of C57BL/6 (H-2$^b$) origin (Ljunggren et al., 1985, J. Exp. Med. 162: 1745–1759). The working examples also employed primary cells and EL4 cells (C57BL/6, H-2$^b$, thymoma).

The cells used in the invention can be maintained in culture according to standard procedures, such as those described by Freshney (1987, Culture of Animal Cells: A Manual of Basic Techniques, 2nd ed. Alan R. Liss, Inc., New York, N.Y.). In the examples below, all cells were maintained in DMEM supplemented with 10% fetal calf serum (FCS), 10 mM Hepes, 2 mM L-glutamine, and 1 mM sodium pyruvate. E.G7-OVA cells were maintained in medium supplemented with 400 μg/ml G418 (GIBCO, Grand Island, N.Y.).

Acid Treatment of Cells: In certain of the examples summarized below, the cells of the invention were compared with cells that were first treated (i.e., washed) with acid and then treated with peptide to increase the density of antigen on the cell surface. In these examples, RMA cells or splenocytes (2×10$^7$ cells) were irradiated, washed, and then gently resuspended in 5 ml of RPMI 1640 supplemented with 25 mM HEPES/5% FCS, adjusted to pH 3.0 with concentrated HCl (see, e.g., Current Protocols in Immunology, Coligan et al., eds. John Wiley & Sons, Inc., New York, N.Y.). The acid-treated cells were centrifuged and immediately resuspended in IMDM medium supplemented with 10% FCS and 10 μM of the desired peptide. Although such a comparison is not necessary for practicing the invention, a comparison of the cells produced according to the invention with cells produced by the acid treatment method provides a convenient indicator of the potency of (i.e., antigen density on) the cells of the invention.

Antigenic Peptides: In practicing the invention, conventional methods can be used to predict, identify, and/or prepare peptides (i.e., antigens or CTL epitopes) that are haplotype matched or mis-matched for the cell that cE is incubated with the peptide (see, e.g., Engelhard, 1994, Current Opinion in Immunology 6:13–23). Generally, a peptide of 6 to 15 amino acids, preferably 8 to 10 amino acids, in length is suitable as an antigen. Examples of antigens presented in various immune responses are provided in Table 2; additional examples are known in the art (see, e.g., Engelhard, supra). Presentation of any of these peptides on the surface of a cell allows the cell to be used to stimulate a CTL response in vitro or in vivo. In the examples described below, a synthetic peptide corresponding to amino acids 257–264 SIINFEKL (H-2K$^b$) (SEQ ID NO: 11) of chicken ovalbumin was used as the haplotype-matched peptide. In addition, synthetic peptides corresponding to CTL epitopes of influenza nucleoprotein were used: amino acids 50–57 SDYEGRLI (H-2K$^k$) (SEQ ID NO: 12), amino acids 147–155 TYQRTRALV (H-2D$^d$) (SEQ ID NO: 13), and amino acids 366–374 ASNENMETM (H-2D$^b$) (SEQ ID NO: 14) (Engelhard, 1994, supra) These peptides have unblocked (i.e., free) amino and carboxyl termini and may be prepared by commercial suppliers (e.g., Research Genetics, Birmingham, Ala.). The peptides were dissolved in serum-free IMDM and stored at −20° C. If desired, other standard cell culture media may be used in the preparation of the peptides. Generally, the AS-treated cells are irradiated prior to "pulsing" the cells with the antigenic peptide. A peptide concentration of 5–100 μM, preferably 5–20 μM (e.g., 10 μM) is suitable for pulsing the cells with peptide. For pulsing the cells with peptide, an incubation period of 1 to 24 hours (e.g., 4 hours), preferably 6 to 12 hours, at 28° C. in medium is appropriate.

μl) at various responder to stimulator (R/S) ratios in 96-well U-bottom tissue culture plates. Effectors were harvested after 5 days of culture on a HISTOPAQUE™ 1083 gradient, which contains ficoll, type 400, and sodium diatrizoate at a density of 1.083 (Sigma, St. Louis, Mo.).

Cytotoxicity Assay: The ability of antigen presenting cells to stimulate a specific CTL response can be measured by assaying the ability of effector cells to lyse target cells. Other commonly used cytotoxicity assays may be substituted for the europium release assays employed in the following working examples. Here, 5–10×10$^6$ target cells were labeled with europium diethylenetriamine pentaacetate for 20 minutes at 4° C. After several washes, 10$^4$ europium-labeled targets and serial dilutions of effector cells at an effector-:target ratio ranging from 50:1 to 6.25:1 were incubated in 200 μl of RPMI 1640 with 10% heat-inactivated FCS in 96-well U-bottom plates. The plates were centrifuged at 500×g for 3 minutes and then incubated at 37° C. in 5% CO$_2$

TABLE 2

| PEPTIDE | | SPECIFICITY | SOURCE | SEQ ID NO |
|---|---|---|---|---|
| AA 257–264 | SIINFEKL | (H-2K$^b$) | chicken ovalbumin | 11 |
| AA 50–57 | SDYEGRLI | (H-2K$^k$) | influenza nucleoprotein | 12 |
| AA 147–155 | TYQRTRALV | (H-2D$^d$) | influenza nucleoprotein | 13 |
| AA 366–374 | ASNENMETM | (H-2D$^b$) | influenza nucleoprotein | 14 |

Induction of OVA-specific CTL in vitro: The cells of the invention can be used to stimulate a CTL response in vitro. In the examples provided below, splenocytes obtained from naive C57BL/6 female retired breeder mice were first treated with ammonium chloride Tris buffer (pH 7.2) for 3 minutes at 37° C. to deplete the sample of red blood cells. The cells then were resuspended in RPMI 1640 supplemented with 10% FCS, 2 mM L-glutamine, 100 IU/ml penicillin, 100 mg/ml streptomycin, 5×10$^{-5}$M β-mercaptoethanol, and 1 mM sodium pyruvate. The sample then was enriched for adherent cells by two 90-minute rounds of adherence at 37° C. Unfractionated splenocytes, adherent cells, and non-adherent cells were treated separately with the oligonucleotide-cationic lipid complexes to generate stimulator cells for induction of CTL responses. B cells were separated from the non-adherent population (B and T cells) by panning on anti-Ig coated plates. The cell population remaining after separation of the B cells was composed of at least 80% T lymphocytes, as judged by FACS analysis. This population of cells was used as the responder T cells.

In the following example, the tumor cell lines and splenocytes were treated with oligonucleotide and LIPOFECTIN™ (1:1 (w/w) DOTMA:DOPE) as described above, washed, and then incubated for 20–24 hours at 28° C. The cells were washed, resuspended in IMDM supplemented with 10% FCS and irradiated at 7,500 rad (for RMA or RMA-S cells) or 3,000 rad (for splenocytes). The cells then were washed once and precultured for 4 hours at 28° C. in IMDM supplemented with 10% FCS, 1 mM sodium pyruvate, 100 IU/ml penicillin, 100 mg/ml streptomycin, 5×10$^{-5}$M β-mercaptoethanol and 10 μM OVA peptide (or control peptide) prior to use as stimulators for CTL induction. Generally, an antigenic peptide concentration of 5–100 μM, preferably 5–20 μM, is suitable.

Naive T cells isolated from C57BL/6 spleens were resuspended in complete IMDM medium at 5×10$^6$ cells/ml and used as responders for primary OVA-specific CTL induction in vitro. A constant number of T cells (5×10$^5$ cells/100 μl) were cultured for 5 days at 37° C. with stimulators (in 100 for 4 hours. A 50 μl aliquot of the supernatant was collected, and europium release was measured by time resolved fluorescence (Volgmann et al., J. Immunol. Methods 119:45–51, 1989). The spontaneous release of europium was less than 25%, and the standard error (SE) of the means of triplicate cultures was less than 5%.

Flow Cytometry Analysis: Cell surface expression of MHC class I molecules can be detected by flow cytometry of cells stained with appropriate antibodies. The working examples set forth below employed the following monoclonal antibodies: purified anti-mouse H-2D$^b$ (clone 28-8.6), FITC conjugated anti-mouse H-2K$^b$ (clone AF6-88.5), FITC conjugated anti-mouse H-2K$^k$ (clone AF3-12.1), and FITC conjugated anti-mouse H-2K$^d$ (SF1-1.1). All of these antibodies are commercially available (e.g., from Pharmingen, San Diego, Calif.). Antibodies for detecting cell surface expression of HLA determinants in humans also are commercially available (e.g., from Becton-Dickinson). The examples also employed a FITC conjugated F(ab')2 fragment of donkey anti-mouse IgG (H+L) (Jackson ImmunoResearch Laboratories, West Grove, Pa.).

In the following working examples, approximately 10$^6$ cells were incubated in PBS containing 3% bovine serum albumin (BSA) with the appropriate concentration of the primary antibody for 30 minutes at 40° C. The cells were washed and, if necessary, incubated for 30 minutes on ice with the secondary antibody, then washed and resuspended in PBS with 3% BSA. As a control, the cells were stained with isotypic antibodies. MHC class I expression was analyzed on a FACScan fluorescence activated cell sorter (Becton Dickinson & Co., Mountain View, Calif.).

Mice: The working examples described below employed five- to seven-week old C57BL/6 mice (H-2$^b$) obtained from Jackson laboratories (Bar Harbor, Me.). When live tumor cells were injected into these mice, these mice provided an animal model of tumorigenesis useful in assaying the ability of the cells of the invention to provide protection against tumor formation. Mice of other haplotypes may also be used in practicing the invention. For example, BALB/c mice provide an H-2$^d$ background, and CBA mice provide an H-2$^k$ background.

The following working examples are provided to illustrate, not limit, the invention.

EXAMPLE I

Inhibition of TAP-2 Function With TAP-2 Antisense Oligonucleotides

Figure 1B:
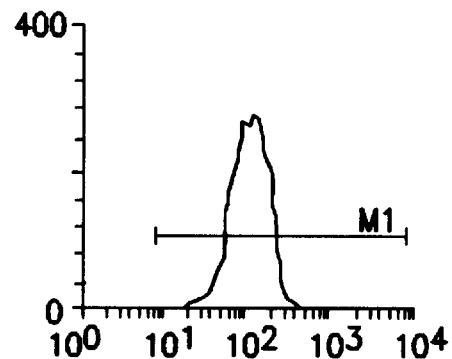
Figure 1C:
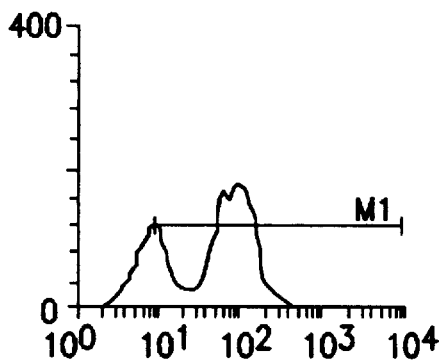
Figure 1D:
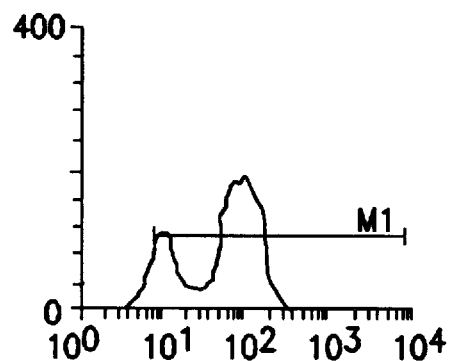
Figure 1E:
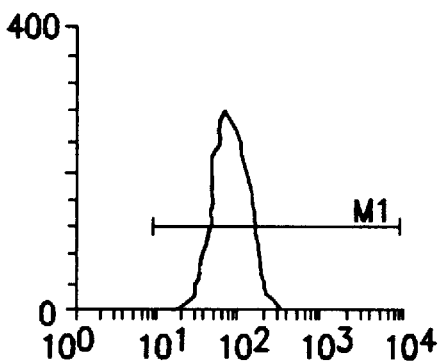
Figure 1F:
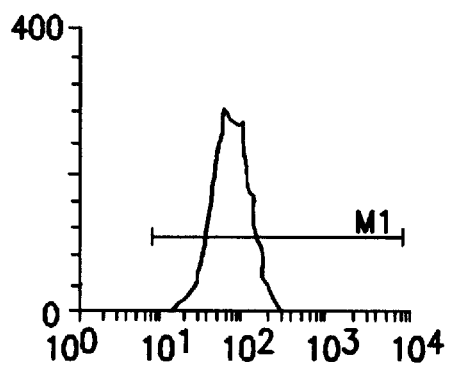

To demonstrate that AS oligonucleotides directed against an MHC class I pathway-associated protein can inhibit gene function and produce a biologically relevant phenotype in cells, we characterized the phenotype of RMA cells transfected with TAP-2 AS oligonucleotides. In an initial experiment, the AS oligonucleotides AS-1, AS-2, AS-3, and AS-4 were introduced, separately, into RMA cells, using the lipid-mediated transfection method described above. Flow cytometry then was used to produce a graph representing cell surface expression of MHC class I molecules on the treated cells. As a negative control, RMA cells were stained with an isotypic antibody (FIG. 1A); a FITC-labeled antibody was used as a positive control (FIG. 1B). The data summarized here provide evidence that approximately 30% of the RMA cells that were treated with AS-1 or AS-2 exhibited a decrease in cell surface expression of MHC class I (FIGS. 1C and 1D, respectively). In contrast, RMA cells that were treated with AS-3 or AS-4 did not exhibit a decrease in MHC class I expression in these experiments, suggesting that they did not destabilize the TAP-2 mRNA (FIGS. 1E and 1F, respectively). Thus, this example illustrates that AS-1 and AS-2 are capable of inhibiting cell surface expression of MHC class I molecules.

Figure 2A:
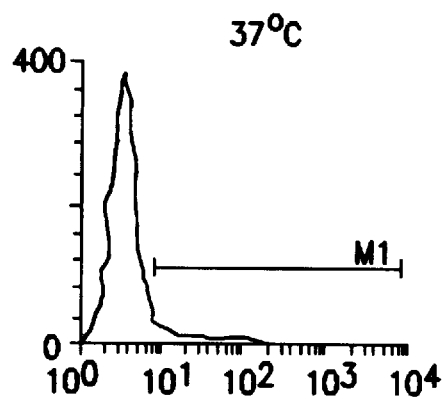
FIGS. 2A–2F are a series of FACS-generated graphs illustrating the effect of temperature on MHC class I expression in RMA cells.
Figure 2B:
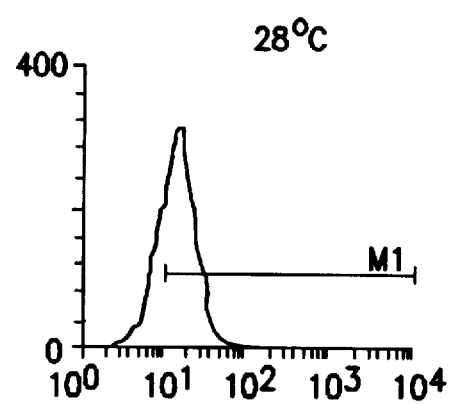
Figure 2C:
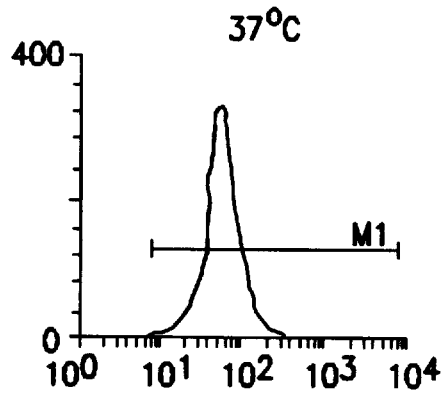
Figure 2D:
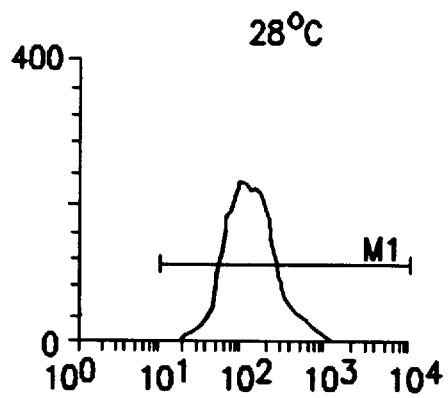
Figure 2E:
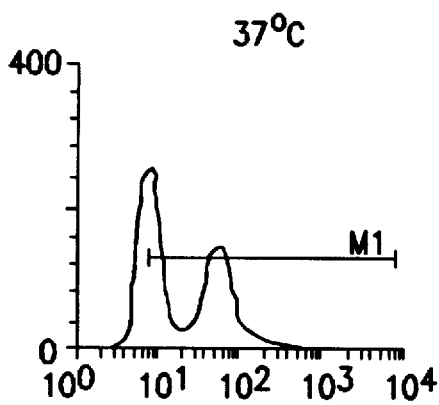
Figure 2F:
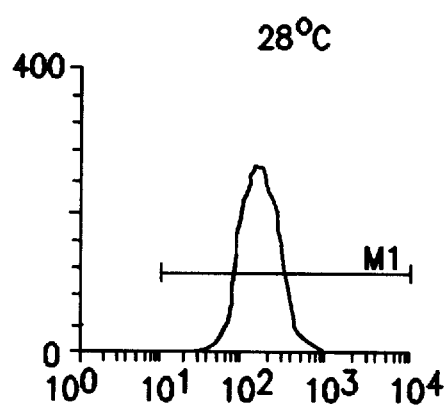

To provide additional evidence that TAP-2 AS oligonucleotides are able to inhibit expression of the TAP-2 gene in a biologically relevant manner, cells treated with TAP-2 AS oligonucleotides were compared with RMA-S cells, a mutant cell line that is deficient in expressing TAP-2 and thus deficient in MHC class I expression. As has previously been reported, when RMA-S cells are grown at 37° C., cell surface expression of MHC class I molecules is essentially undetectable (FIG. 2A) (Ljunggren et al., 1990, Nature 346:476–480). However, MHC class I expression can be restored in RMA-S cells by growing them at a reduced temperature (FIG. 2B). In contrast to MHC expression in the mutant cell line, expression of MHC class I molecules on wild-type RMA cells does not differ at the two temperatures (FIGS. 2C and 2D). The data provided herein demonstrate that wild-type RMA cells that are treated with the TAP-2 antisense oligonucleotide AS-1 exhibit a phenotype that is comparable to that of the TAP-2 deficient RMA-S cells. In this example, 50–55% of the RMA cells treated with AS-1 exhibited a decrease in MHC class I expression at 37° C. (FIG. 2E). As is the case for the TAP-2 deficient RMA-S cells, restoration of MHC class I expression in AS-1-treated RMA cells is restored by growing the cells at 28° C. (FIG. 2F). Accordingly, these data provide evidence that a TAP-2 AS oligonucleotide can be used to inhibit expression of MHC class I molecules on the surface of RMA cells.

Figure 3A:
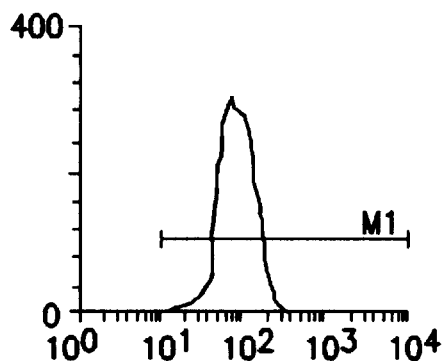
FIGS. 3A–3F are a series of graphs representing MHC class I expression on cells incubated with MHC restricted peptides.
Figure 3B:
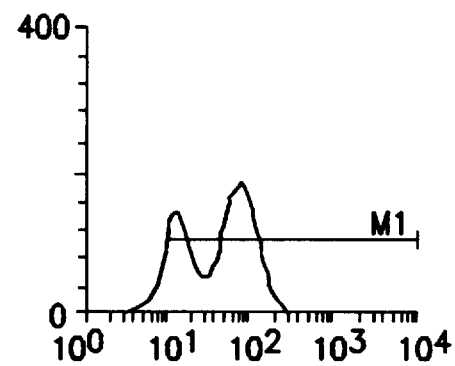
Figure 3C:
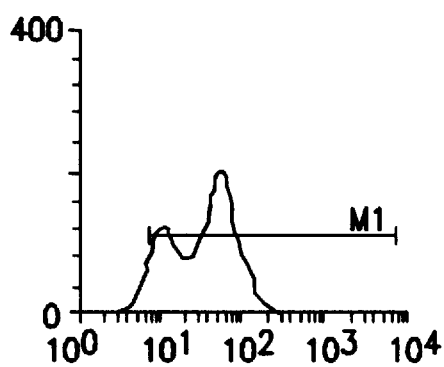
Figure 3D:
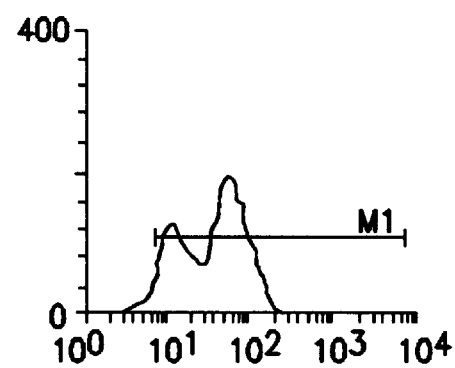
Figure 3E:
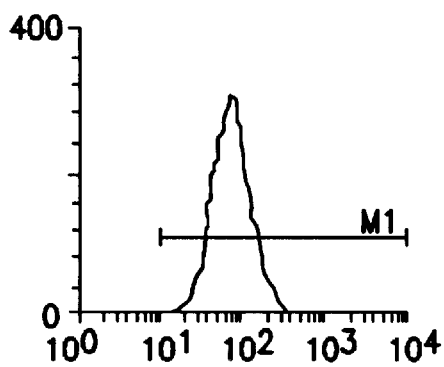
Figure 3F:
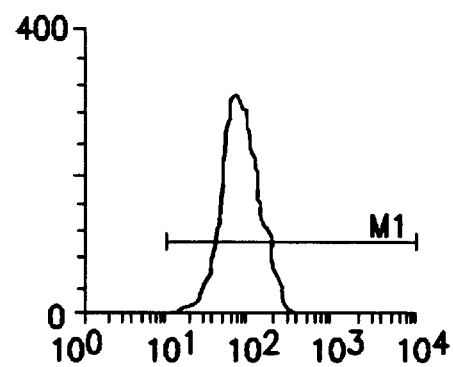

In yet another assay, we demonstrated that, as is the case for MHC class I expression on RMA-S cells, MHC class I expression on AS-1-treated RMA cells can be restored by contacting the cells with an MHC haplotype-matched peptide. In this example, MHC class I expression on RMA cells grown at 37° C. and treated with AS-1 was decreased by approximately 40% (FIG. 3B). The control AS oligonucleotide, CON-1, had no effect on MHC expression (FIG. 3A). Incubation of AS-1-treated RMA cells with the haplotype-mismatched peptides NP (H-2K$^d$) (FIG. 3C) or NP (H-2K$^k$) (FIG. 3D) did not restore MHC class I expression. In contrast, incubation of AS-1-treated RMA cells with the haplotype-matched peptides NP (H-2D$^b$) (FIG. 3E) or NP (H-2K$^b$) (FIG. 3F), did restore MHC class I expression. In sum, the data set forth above demonstrate that treatment of RMA cells with the TAP-2 AS oligonucleotides confers a phenotype on the cells that closely resembles that of RMA-S cells, a TAP-2 mutant cell line.

EXAMPLE II

Figure 4A:
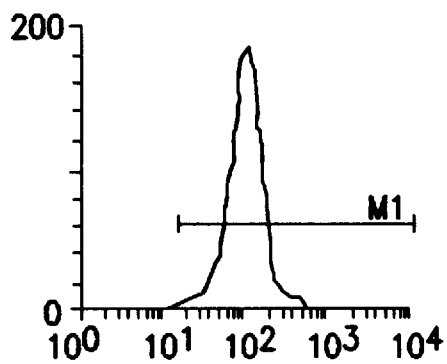
FIGS. 4A–4F are a series of graphs depicting MHC class I expression on EL4 cells.
Figure 4B:
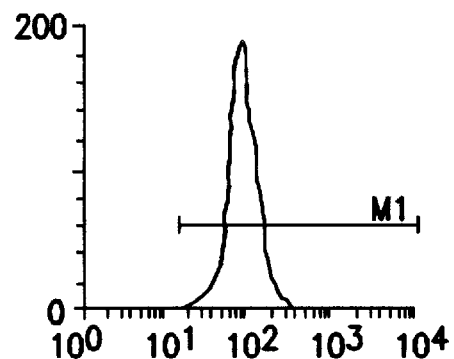
Figure 4C:
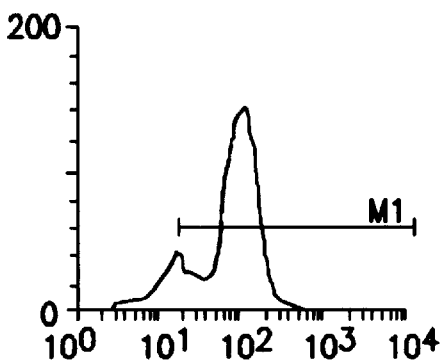
Figure 4D:
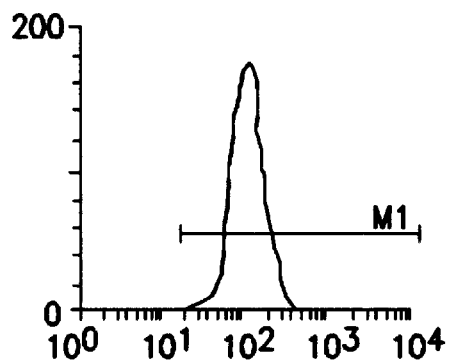
Figure 4E:
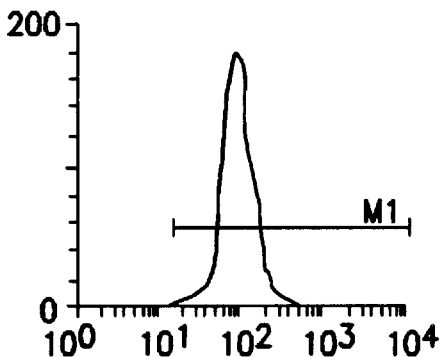
Figure 4F:
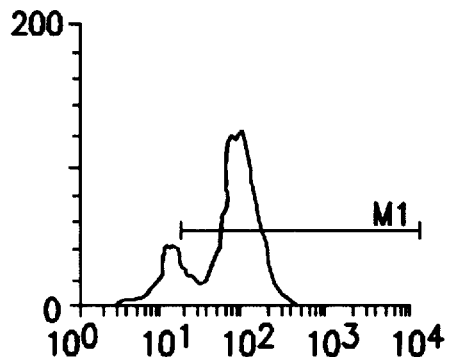

Use of TAP-2 AS Oligonucleotides to Inhibit MHC Class I Expression on EL4 Cells This working example provides evidence that AS oligonucleotides can also be used to inhibit MHC class I expression on the surface of EL4 cells, an established thymoma cell line of C57EL/6 origin (H-2$^b$). Treatment of EL4 cells with AS-1 resulted in a reduction in MHC class I expression in 30 to 60% of the cells (compare FIG. 4C with FIG. 4A). In contrast, treatment of EL4 cells with CON-1, the control oligonucleotide, did not affect MHC class I expression (compare FIG. 4B with FIG. 4A). In addition, this example demonstrates that cell surface expression of MHC class I molecules on AS-1 treated EL4 cells could be restored by incubating the cells at 28° C. (FIG. 4D). MHC class I expression could also be restored by contacting the cells with the haplotype-matched peptide OVA H-2K$^b$ (FIG. 4E), while treatment of the cells with the haplotype mis-matched peptide, NP H-2K$^k$ did not restore MHC class I expression (FIG. 4F). In sum, these data show that a TAP-2 AS oligonucleotide is able to inhibit MNC class I expression on a second cell type.

EXAMPLE III

Figure 5A:
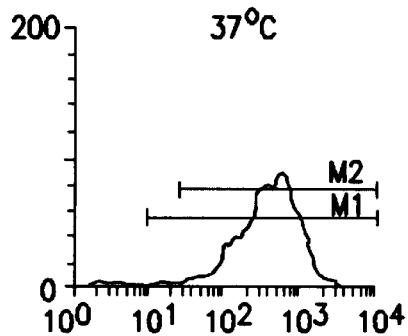
FIGS. 5A–5H are a series of graphs depicting MHC class I expression in splenocytes from C57BL/6 mice.
Figure 5B:
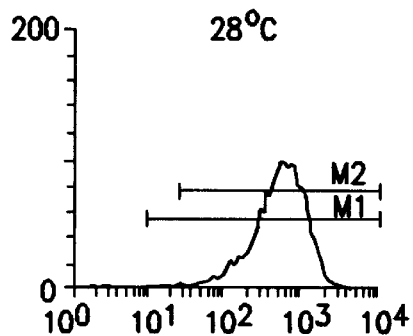
Figure 5C:
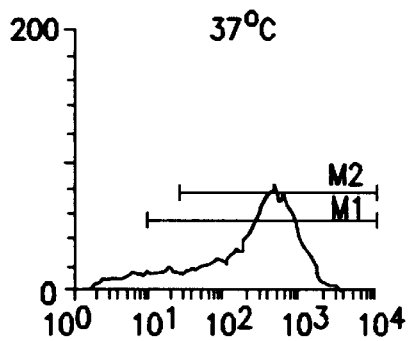
Figure 5D:
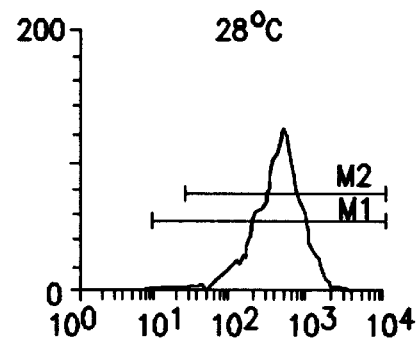

Use of TAP-2 Antisense Oligonucleotides to Inhibit MHC Expression on Primary Cells The following data provide evidence that AS oligonucleotides can be used to inhibit MHC expression on the surface of primary cells. In this example, splenocytes were isolated from C57BL/6 mice and incubated at 37° C. or 28° C. (FIGS. 5A and 5B, respectively). Approximately 30% of the C57BL/6 cells that were treated with AS-1 at 37° C. exhibited a decrease in MHC class I expression (FIG. 5C). As was the case for MHC expression on RMA cells and EL4 cells, expression of MHC class I molecules could be restored by growing the cells at 28° C. (FIG. 5D).

Figure 5E:
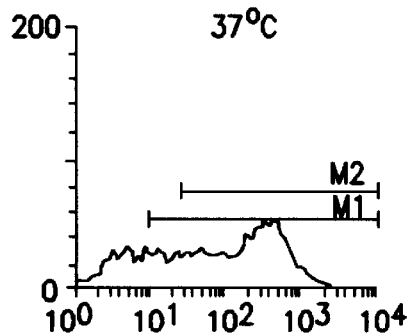
Figure 5F:
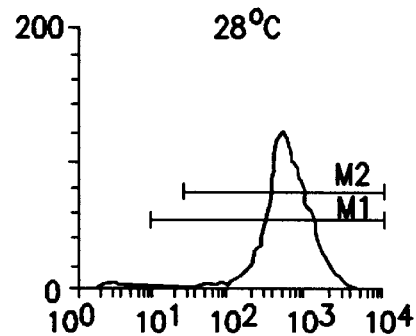
Figure 5G:
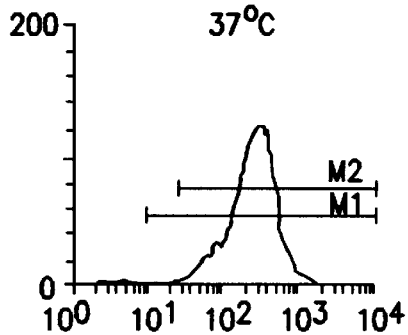
Figure 5H:
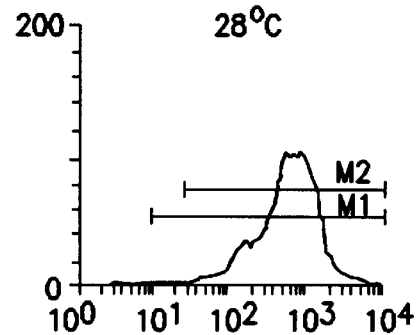

To determine whether AS-1 inhibited MHC expression more efficiently in certain splenocytes than in others, the sample of splenocytes was fractionated into adherent and non-adherent populations, as described above. The adherent population was composed primarily of antigen-presenting cells such as monocytes/macrophages and dendritic cells. The non-adherent population was composed of T and B lymphocytes. Of the adherent population, over 50% of the cells showed a decrease in MHC class I expression when treated with AS-1 (FIG. 5E). As is the case for MHC expression on the other AS-1 treated cells and RMA-S cells, cell surface MHC expression could be restored in these AS-1 treated adherent cells by incubating them at 28° C. (FIG. 5F). MHC class I expression on non-adherent cells was also inhibited by AS-1, although a smaller percentage of the cells were affected (FIG. 5G). Incubation of these AS-1 treated non-adherent cells at 28° C. also restored MHC class I expression (FIG. 5H). The difference in inhibition of TAP-2 in adherent cells versus non-adherent cells is thought to be due to the difference in their ability to take up the AS oligonucleotides, with cells in the adherent fraction being more phagocytic, and thus likely to take up more of the AS oligonucleotide than are non-adherent cells. These experiments demonstrate that AS-1-treated primary splenocytes, and adherent cells in particular, display a phenotype that is comparable to that of cells that are deficient in their ability to express TAP-2. These results also indicate that primary cells isolated from a mammal (e.g., a human) can be engineered to be potent antigen-presenting cells. indeed, we also observed a similar down regulation of MHC expression when human precursor-derived dendritic cells were treated with TAP-1 or TAP-2 AS oligonucleotides having the sequences of SEQ ID NOs: 3, 4, 5, or 6.

EXAMPLE IV

Use of AS Oligonucleotide-treated RMA Cells to Induce a CTL Response In Vitro

Figure 6:
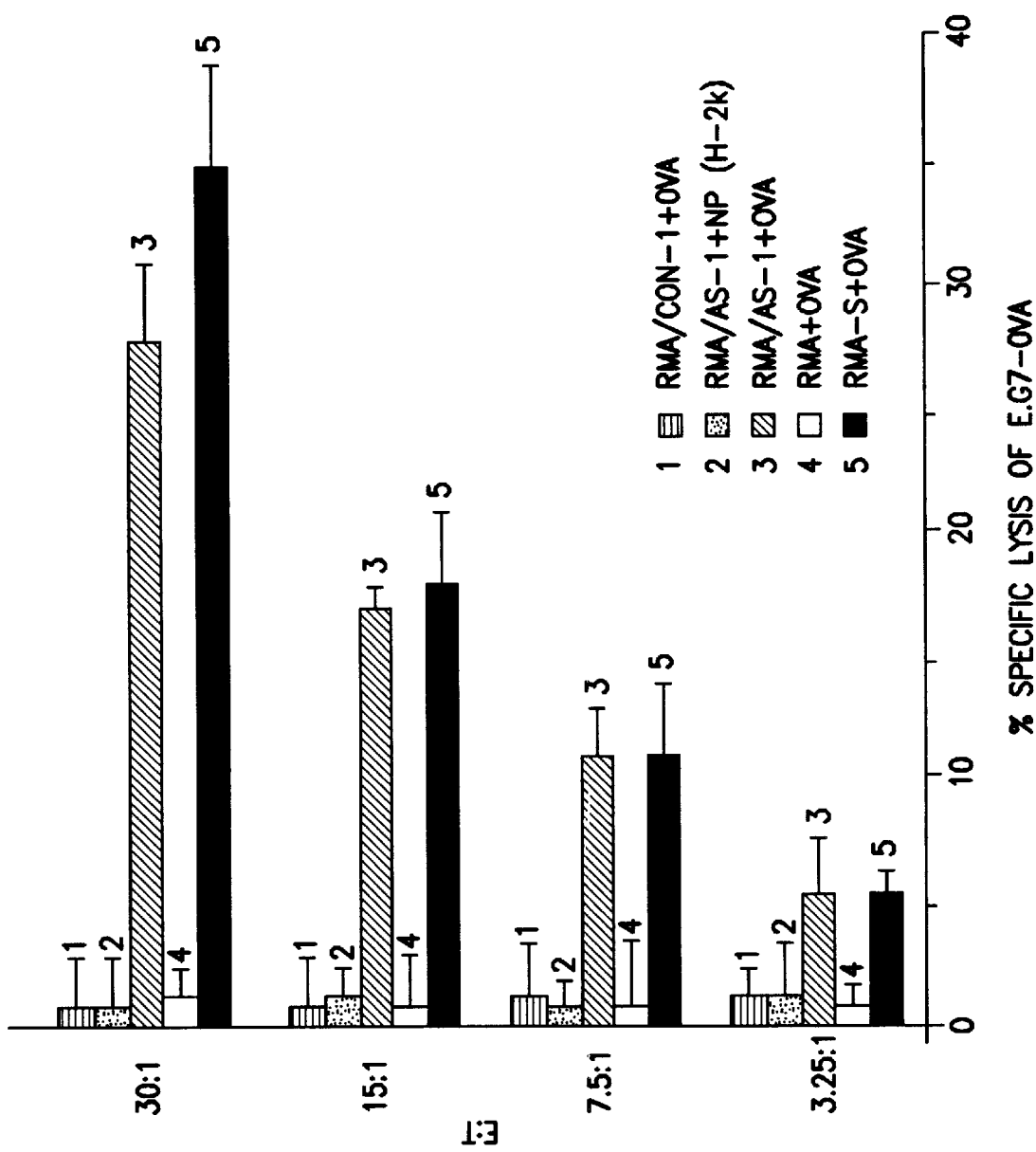
FIG. 6 is a histogram representing OVA-specific CTL responses over a range of effector:target ratios. Bar 1 represents CON-1 treated RMA cells incubated with a haplotype matched OVA peptide. Bar 2 represents AS-1 treated RMA cells incubated with the haplotype mis-matched peptide NP (H-2K$^k$). Bar 3 represents AS-1 treated RMA cells incubated with the haplotype matched OVA peptide (H-2K$^b$). Bar 4 represents untreated RMA cells incubated with the haplotype matched OVA peptide. Bar 5 represents the TAP-2 deficient RMA-S cells incubated with the haplotype matched OVA peptide.

The following example demonstrates that cells that are treated with TAP AS oligonucleotides and then incubated with haplotype-matched peptides serve as potent stimulators of a CTL response in viltro. In this example, splenocytes were treated with AS-1 and then incubated at 28° C. with an ovalbumin (OVA) peptide, as is described above. These cells were used as stimulators at a responder:stimulator ratio of 4:1. The resulting effector cells then were assayed for their ability to lyse target cells expressing an OVA peptide. In this case, the target cells were E.G7-OVA cells, which are EL4 cells transfected with the OVA gene. These assays were performed at four different ratios of effector:target cells. As a positive control, the TAP-2-deficient RMA-S cells were incubated with the haplotype-matched OVA peptide and then used as stimulators. At each effector:target ratio, the AS-1 treated RMA cells incubated with the haplotype-matched OVA peptide stimulated a potent CTL response (FIG. 6, bar 3) that is comparable to the response produced by RMA-S cells (FIG. 6, bar 5). In contrast, no CTL response was induced by (a) RMA cells that were treated with the control oligonucleotide CON-1 and the OVA peptide (FIG. 6, bar 1), (b) RMA cells that were treated with AS-1 and an influenza nucleoprotein peptide (FIG. 6, bar 2), or (c) RMA cells that were treated with the OVA peptide but not treated with an AS oligonucleotide (FIG. 6, bar 4). As an additional control, EL4 cells were used as targets, and no CTL activity was detected. In sum, this example demonstrates that the invention provides an efficient method for inducing a CTL response in vitro.

EXAMPLE V

Figure 7:
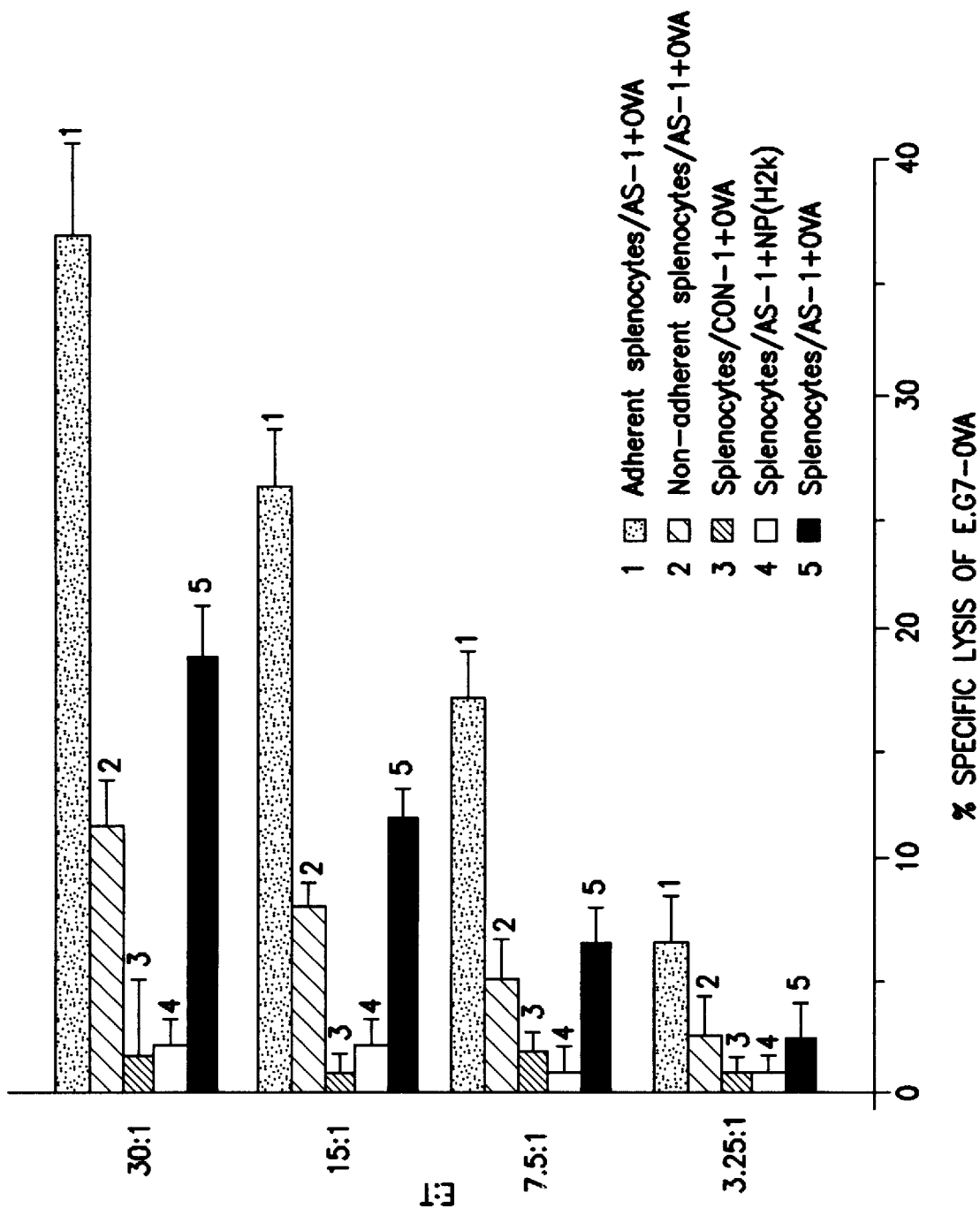
FIG. 7 is a histogram representing OVA-specific CTL responses induced by antigen-presenting splenocytes from C57BL/6 mice. Bar 1 represents the response obtained with AS-1 treated adherent splenocytes incubated with the haplotype matched OVA peptide. Bar 2 represents the response obtained with AS-1 treated non-adherent splenocytes incubated with the haplotype matched OVA peptide. Bar 3 represents the response obtained with CON-1 treated unfractionated splenocytes incubated with the haplotype matched OVA peptide. Bar 4 represents the results obtained with AS-1 treated unfractionated splenocytes incubated with the haplotype mis-matched NP (H-2K$^k$) peptide. Bar 5 represents the response obtained with AS-1 treated unfractionated splenocytes incubated with the haplotype matched OVA peptide.

Use of AS Oligonucleotide-treated Primary Splenocytes to Induce a CTL Response In Vitro The following example demonstrates that primary splenocytes treated with AS oligonucleotides also serve as potent stimulators of CTL responses. Here, splenocytes were treated with AS-1 then incubated with the OVA peptide. The stimulated CTL then were assayed for their ability to lyse E.G7-OVA colls at four different effector:target ratios. In addition, the adherent and non-adherent fractions of splenocytes were assayed for the ability to stimulate CTL. Adherent splenocytes treated with AS-1 and incubated with a haplotype-matched OVA peptide were potent stimulators of CTL (FIG. 7, bar 1). Unfractionated splenocytes and non-adherent splenocytes treated with AS-1 and the OVA peptide also were able to stimulate a CTL response (FIG. 7, bars 5 and 2, respectively). In contrast, splenocytes treated with (a) the control oligonucleotide CON-1 and the OVA peptide or (b) AS-1 and an influenza nucleoprotein peptide did not significantly stimulate CTL (FIG. 7, bars 3 and 4, respectively). Thus, these experiments provide evidence that primary cells can be used in the invention to produce antigen-presenting cells that induce a CTL response in vitro.

EXAMPLE VI

Comparison of AS Oligonucleotide-treated Cells with Acid-Treated Cells

Figure 8A:
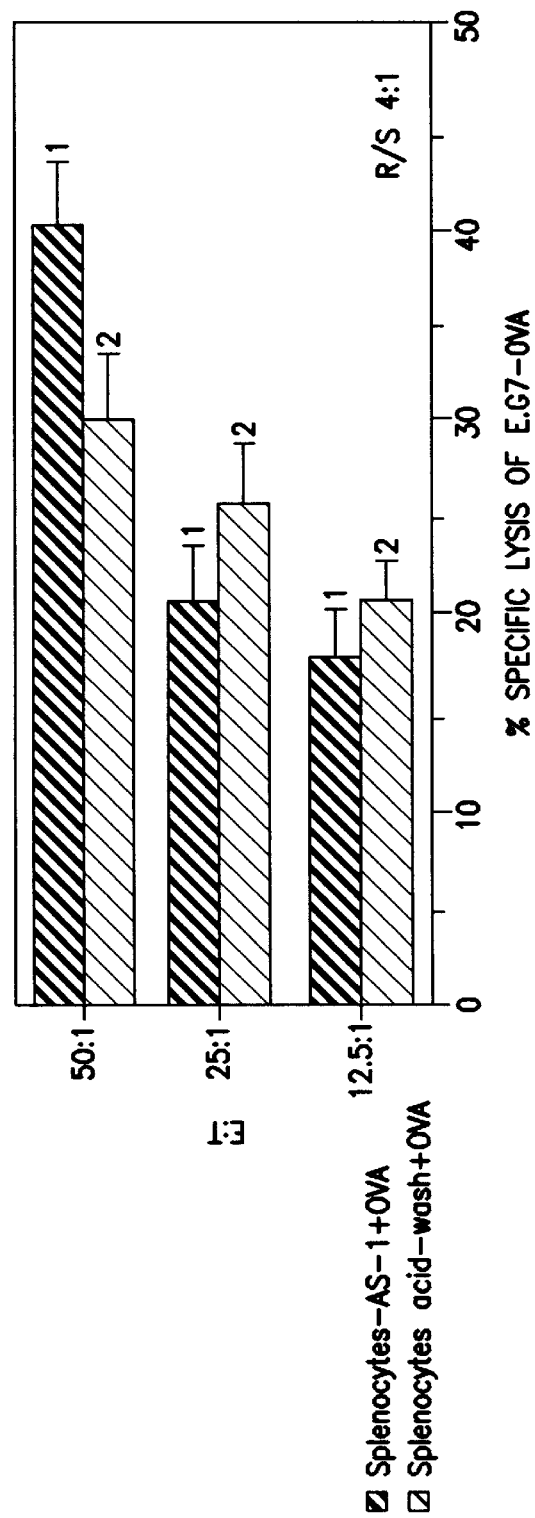
FIGS. 8A–8B are a pair of histograms representing CTL responses obtained with AS-1 treated splenocytes incubated with a haplotype matched OVA peptide (bar 1), or acid-treated splenocytes incubated with a haplotype matched OVA peptide (bar 2).
Figure 8B:
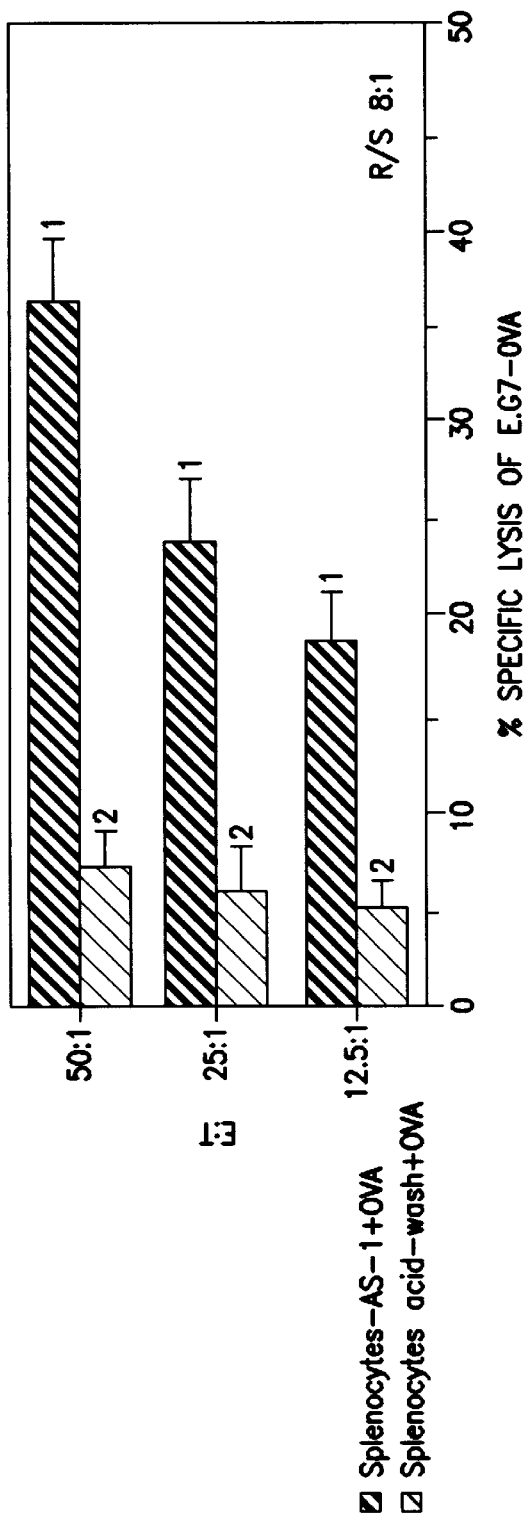

A previously described method to increase the density antigen on the surface of cells employs a mild acid wash to remove the resident peptides bound to MHC class I molecules. The resident peptides are then replaced with preferred antigenic peptides (Langlade-Demoyen et al., International Immunology 6:1759–1766, 1994). These acid-treated cells are able to stimulate a primary CTL response in vitro. Using acid-treated cells prepared as described above, we made a comparative assessment of the antigen-presenting capabilities of cells treated with TAP AS oligonucleotides. These experiments were performed at two different responder:stimulator ratios: (a) 8:1 ($5 \times 10^5$ naive T cells mixed with $6.125 \times 10^4$ splenocytes), and (b) 4:1 ($5 \times 10^5$ naive T cells mixed with $1.25 \times 10^5$ splenocytes). The ratio of effector:target cells ranged from 12.5:1 to 50:1. As in other examples, the target cells were E.G7-OVA cells, which express OVA peptides. At a responder:stimulator ratio of 4:1, the AS-1 treated cells were more effective than, or comparable to, the acid treated cells in stimulating a CTL response (FIG. 8A). At a responder:stimulator ratio of 8:1, the acid-treated cells showed a decreased ability to stimulate a CTL response (FIG. 8B, bar 2), while the AS-1 treated cells remained potent stimulators (FIG. 8B, bar 1). Overall, these data provide evidence that cells treated with a TAP-2 antisense oligonucleotide are more effective than acid-treated cells in stimulating a CTL response, indicating that the antigen presenting cells of the invention have a high density of antigen.

EXAMPLE VII

Use of AS-1-Treated Cells to Generate a CTL Response In Vivo

We have discovered that cells treated with a TAP AS oligonucleotide and an appropriate peptide are able to stimulate a CTL response in vivo and provide protective immunity in an animal model of disease. Tumor cell lines and cells in the adherent fraction of primary splenocytes were washed and treated with AS-1 or control oligonucleotides and LIPO-FECTIN™ (1:1 (w/w) DOTMA:DOPE) as described above. The cells were then washed and resuspended in IMDM containing 10% FCS, and then irradiated at 20,000 rad (for E.G7-OVA and EL4 cells), 7,500 rad (for RMA cells), or 3,000 rad (for splenocytes). The cells were washed once and incubated with the OVA peptide or the control peptide NP (H-$2D^b$) for 4 hours at 28° C. in IMDM supplemented with 10% FCS and 1 mM sodium pyruvate. After 4 hours, the cells were washed twice and resuspended in PBS before being injected into mice. To immunize naive, syngeneic C57BL/6 mice, $2 \times 10^6$ AS-1 and OVA peptide treated RMA cells or splenocytes in 500 µl PBS were injected into each mouse. E.G7-OVA and EL4 cells were injected at a level of $5 \times 10^6$ cells per mouse.

After 7–10 days, splenocytes of the immunized mice were harvested, and the samples were depleted of red blood cells. Subsequently, $1.5 \times 10^7$ splenocytes were cultured with 1×10⁶ irradiated E.G7-OVA stimulator cells (20,000 rad) in 5 ml of IMDM with 10% FCS, 1 mM sodium pyruvate, 100 IU/ml penicillin, 100 mg/ml streptomycin, and 5×10⁻⁵M β-mercaptoethanol per well in a 6-well tissue culture plate. The cells were incubated for 5 days at 37° C. in 5% $CO_2$, and effectors were harvested on day 5 on a HISTOPAQUE™ 1083 gradient, which contains ficoll, type 400, and sodium diatrizoate at a density of 1.083 (Sigma, St. Louis, Mo.).

AS-1 treated adherent splenocytes incubated with OVA peptide induced high levels of lysis of E.G7-OVA target cells (FIG. 9, line 4). In addition, immunization with 2×10⁶ AS-1 treated adherent splenocytes was more effective than immunization with 5×10⁶ E.G7-OVA cells (FIG. 9, compare lines 4 and 3), indicating that adherent splenocytes are more potent than are E.G7-OVA cells and suggesting that the density of antigen is higher on adherent splenocytes than on E.G7-OVA cells. AS-1 treated RMA cells incubated with the haplotype matched OVA peptide also were strong stimulators of a CTL response (FIG. 9, line 9). The CTL response generated by these cells was comparable to the responses generated by E.G7-OVA cells (FIG. 9, line 3) and acid-treated adherent splenocytes incubated with the OVA peptide (FIG. 9, line 7). A weak CTL response was produced with adherent splenocytes that were treated with the control oligonucleotide CON-1 then incubated with the OVA peptide (FIG. 9, line 6). This response is likely due to the antigen-presenting capabilities of the macrophages and dendritic cells present at high levels in the adherent cell population. No significant CTL response was detected in mice that were immunized with EL4 cells, PBS, or cells incubated with the control peptide NP ($H-2D^b$). Overall, these experiments demonstrate that cells that are treated with AS oligonucleotides directed against an MHC class I pathway-associated protein and subsequently incubated with haplotype matched antigenic peptides can be used to stimulate a CTL response in vivo.

EXAMPLE VIII

Use of AS-treated Cells to Provide Immunoprotection In Vivo

The following in vivo experiments provide evidence that antigen-presenting cells of the invention provide protection against tumor challenge. In these experiments, C57BL/6 mice were immunized once with 2×10⁶ irradiated AS-1 treated adherent splenocytes or RMA cells, or with 5×10⁶ E.G7-OVA or EL4 cells. At ten days post-immunization, mice were challenged with 2×10⁷ live E.G7-OVA cells injected subcutaneously into the flank region; this dosage of live tumor cells is capable of causing tumors in non-immunized mice. Mice were monitored for tumor growth and tumor size, and mice having tumors 3.5 cm in diameter were sacrificed. All survivors were sacrificed at 40 days post-challenge.

Figure 10A:
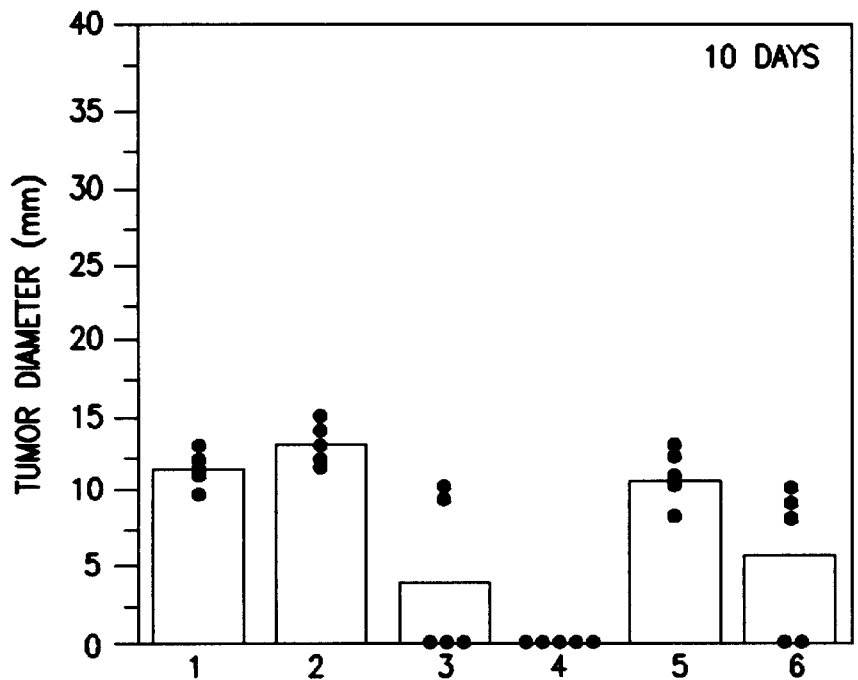
FIGS. 10A–10B are a pair of histograms representing tumor size at 10 and 35 days, respectively, in C57BL/6 mice challenged with a tumorigenic dose of live E.G7-OVA cells. Mice represented by each dot in the figure were inoculated with PBS (bar 1), EL4 cells (bar 2), E.G7-OVA cells (bar 3), AS-1 treated adherent splenocytes incubated with a haplotype matched OVA peptide (bar 4), AS-1 treated adherent splenocytes incubated with a haplotype mis-matched NP peptide (bar 5), or AS-1 treated RMA cells incubated with a haplotype matched OVA peptide (bar 6).

As negative controls, mice were inoculated with (a) PBS, (b) EL4 cells, or (c) adherent splenocytes treated with AS-1 and an influenza nucleoprotein (NP) peptide. Within 10 days, all 5 of the mice in each of the negative control groups (PBS, EL4 cells, and Adh.splen./AS-1+NP; FIG. 10A, bars 1, 2, and 5) developed tumors from of 3 to 3.5 cm in diameter. In contrast, protection from tumor challenge was evident in all five mice that were immunized with adherent AS-1 treated splenocytes that had been incubated with a haplotype-matched OVA peptide (FIG. 10A, bar 4). Four of these five mice (represented by dots in the figure) were completely protected from tumor challenge during the course of the 35-day study (FIG. 11B, bar 4). The tumor in the fifth protected mouse developed slowly, reaching only half the size of the tumors of the unprotected mice.

Figure 10B:
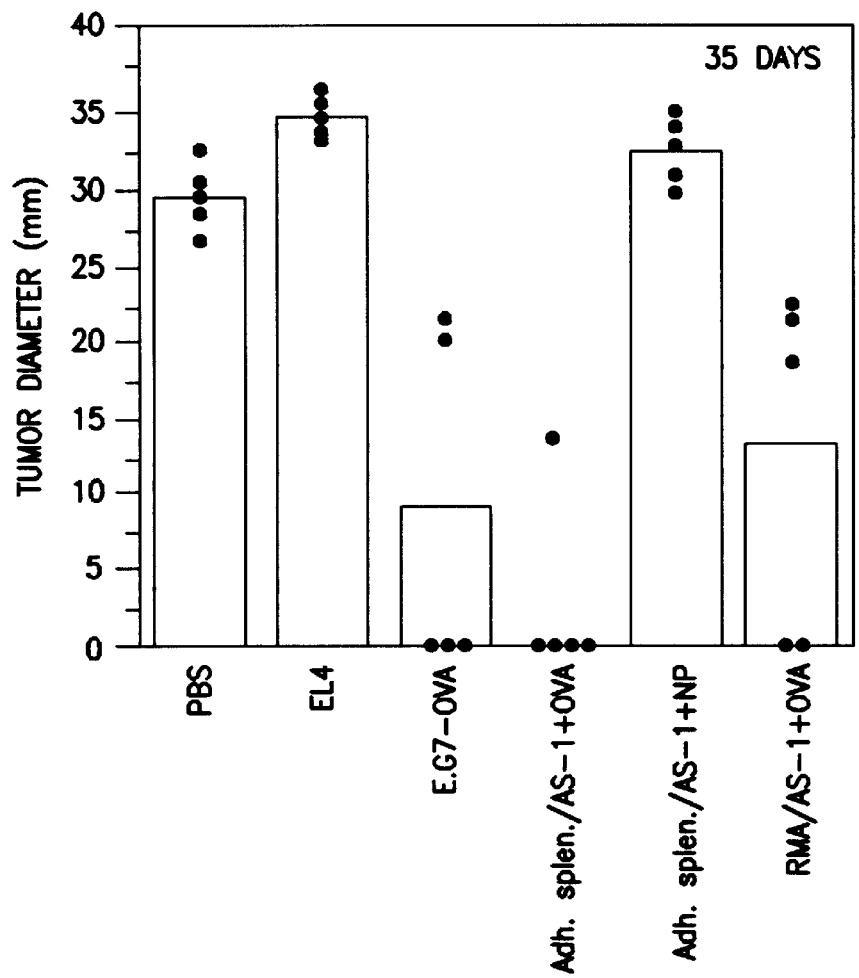

Protection against tumor challenge was also evident for mice that were immunized with AS-1-treated RMA cells that had been incubated with a haplotype-matched OVA peptide (FIGS. 10A and 10B, bar 6). Two of these five mice were completely protected against tumor formation. At 35 days, the tumors that developed in the remaining three (FIG. 10B, bar 6) mice were substantially smaller than the tumors of control mice (FIG. 10B, bars 1, 2, and 5). As was the case in the in vitro experiments, the treated adherent splenocytes generated the most potent immune response in vivo. These data provide evidence of a correlation between the in vitro and in vivo results. In this example, 2×10⁶ AS-1 treated adherent splenocytes again are more effective than are 5×10⁶ E.G7-OVA cells (compare FIGS. 10A and 10B, bars 3 and 4), even though E.G7-OVA cells are highly immunogenic and able to induce immunity against tumor challenge. Generally, a single immunization with 10⁵ live E.G7-OVA cells, or three immunizations with 5×10⁶ irradiated cells, elicits a strong CTL response and provides complete protection from tumor challenge with 2×10⁷ live E.G7-OVA cells. In sum, these experiments demonstrate that cells that are treated with AS oligonucleotides that inhibit expression of an MHC class I and which subsequently are incubated with a haplotype-matched peptide are potent stimulators of CTL responses in vivo. Using this animal model of tumorigenesis, the cells of the invention inhibited or completely prevented tumor formation.

EXAMPLE IX

Use of a Proteasome Inhibitor in Producing an Antigen Presenting Cell

This example demonstrates that a proteasome inhibitor can be used to inhibit the activity of an MHC class I pathway-associated component in the production of potent antigen presenting cells. In this example, the activity of an MHC class I pathway-associated component was inhibited by contacting 2.5–5.0×10⁶ precursor-derived dendritic cells for 1 hour in 1 ml in a 24-well plate with the proteasome inhibitor MG132 at a concentration of 700 nM (Myogenics, Inc., Cambridge, Mass.). The cells subsequently were contacted with antigenic peptide at a concentration of 50 μg/ml and β2 microglobulin (3 μg/ml) for 3–6 hours, thereby producing antigen presenting cells. In this example, the peptide had the amino acid sequence CINGVCWTV (SEQ ID NO: 15), which corresponds to amino acids 1077–1085 of the NS3 protein of hepatitis C virus (HCV). The resulting antigen presenting cells are referred to as DC/MG132+HCV pep.

For comparison, antigen presenting cells also were produced by using the HCV peptide to contact precursor-derived dendritic cells that had not been exposed to the proteasome inhibitor. The resulting cells are referred to as DC+HCV pep. Also, for comparison, antigen presenting cells were produced by contacting precursor-derived dendritic cells with an Epstein Barr virus (EBV) peptide having the amino acid sequence CLGGLLTMV (SEQ ID NO: 16), which corresponds to amino acids 426–434 of LMP2A protein. As above, 2.5–5.0×10⁶ cells were used and the peptide was used at 50 μG/ml. The resulting cells are referred to as DC+EBV pep. In each case, the precursor-derived dendritic cells were pulsed with peptide in the presence of 3 μg/ml β2-microglobulin. Although the β2 microglobulin is optional, it is preferred that β2 microglobulin be included.

The various antigen presenting cells (DC/MG132+HCV pep, DC+HCV pep, and DC+EBV pep) were used, separately, as stimulators in the induction of primary CTL. The PBMC used to produce CTL were obtained from HLA-A2 individuals and were autologous to the precursor-derived dendritic cells that had been contacted with antigenic peptide. CTL induction was performed by contacting PBMC at a responder:stimulator ratio of 10:1 in the presence of 10 ng/ml IL-7 and 20 U/ml IL-2. Cells were expanded for twelve days, and on day 12, $CD8^+$ cells were selected and cultured in the presence of IL-2 (20 U/ml) for 48 hours. On day 14 $CD8^+$ blasts were re-stimulated at a responder:stimulator ratio of 10:1 in the presence of IL-7 and IL-2. After a total of 20 days of culturing the cells (at 37° C.), CTL were assayed for their ability to lyse target cells.

In the CTL assays, the target cells were T2 cells that had been pulsed with 50 μg/ml of HCV peptide (FIG. 11A) or 50 μg/ml EBV peptide (FIG. 11B) (see Salter et al., Immunogenetics 21:235–246). Dendritic cells that were contacted with MG132 and HCV peptide (DC/MG132+HCV pep) stimulated a more potent CTL response against target cells that contained the HCV peptide than did dendritic cells that were not contacted with MG132 (DC+HCV pep; FIG. 11A). The negative control cells (DC+EBV pep) did not stimulate a significant CTL response. As is desired, the CTL response generated by the cells is specific for the antigenic peptide used to pulse the cells. When target cells containing EBV peptide were used, dendritic cells that were pulsed with EBV peptide (DC+EBV pep) stimulated a CTL response, whereas dendritic cells that were pulsed with HCV peptide (DC/MG132+HCV pep and DC+HCV pep) did not stimulate a significant CTL response (FIG. 11B). In sum, this example demonstrates that a potent antigen presenting cell can be produced by (i) inhibiting an MHC class I pathway-associated component by contacting a cell with a proteasome inhibitor and (ii) contacting the cell with an antigenic peptide. Such a cell can be used to stimulate a potent antigen specific CTL response.

Use

The invention provides a method for generating a cell that bears a preferred antigen at an increased density on its surface, and such cell can be used to stimulate a potent CTL response. The comparative assays summarized above suggest that the antigen is present at a high density on the cells of the invention. Generally, an antigen that constitutes greater than 10%, preferably greater than 20%, of all peptides on an antigen presenting cell is considered to be present at a high density. The antigen-presenting cell(s) produced with the invention can be used to stimulate a CTL response in vitro or in vivo. Where the antigen-presenting cell of the invention is administered to a mammal, the cell is useful for eliciting a cell-mediated immune response to the cell surface antigen, and thus the antigen-presenting cell can be used as a vaccine or a therapeutic in treating a wide variety of disease states. Thus, the invention includes, but is not limited to, methods for treating cancers (e.g., malignant tumors or carcinomas such as melanomas, breast cancers, and colorectal cancers). Also included are methods for treating a mammal infected with a pathogen such as a bacterium (e.g., Salmonella, Shigella, or Enterobacter) or a virus (e.g., a human immunodeficiency virus, a Herpes virus, an influenza virus, a poliomyelitis virus, a measles virus, a mumps virus, or a rubella virus).

In treating a mammal afflicted with a disease or infection, it is not required that the cell that is administered to the mammal be derived from the mammal. Thus, the antigen-presenting cell can be obtained from a matched donor, or from a culture of cells grown in vitro. Methods for matching haplotypes are known in the art.

It is preferable that treatment begin before or at the onset of disease or infection, and continue until the disease or infection is ameliorated. In treating a mammal with a cell or vaccine produced according to the invention, the optimal dosage of the vaccine or cells depends on factors such as the weight of the mammal, the severity of the disease, and the strength of the CTL epitope. Prior to administration of cells that were maintained in vitro, the cells generally are washed with PBS to remove the culture medium. Generally, a dosage of $10^5$ to $10^8$ cells/kg body weight, preferably $10^6$ to $10^7$ cells/kg body weight, is administered in a pharmaceutically acceptable excipient to the patient. The antigen-presenting cells can be administered using infusion techniques commonly used in cancer therapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

Where the antigen presenting cell is used to induce a CTL response in vitro, the resulting effector CTLs can subsequently be administered to a mammal in a CTL-based method of therapy (see, e.g., PCT/US91/06441). CTL produced in vitro with the antigen presenting cells of the invention can be administered in a pharmaceutically acceptable excipient to a mammal by employing conventional infusion methods (see, e.g., Rosenberg et al., supra). Typically, $10^9$–$10^{10}$ cells are administered over the course of 30 minutes, with treatment repeated as necessary. Such a CTL-based method of therapy may be combined with other methods, such as direct administration of the antigen presenting cells of the invention. The CTL and antigen presenting cells may be autologous or heterologous to the mammal undergoing therapy. If desired, the treatment may also include administration of mitogens (e.g., phytohemagglutinin) or lymphokines (e.g., IL-2, IL-2, and/or IL-4) to enhance CTL proliferation.

What is claimed is:

1. A method of increasing the presentation of a peptide on a mammalian cell, said method comprising inhibiting activity of an MHC class I pathway-associated component in said cell in vitro prior to contacting said cell with said peptide, wherein said MHC class I pathway-associated component is a TAP protein or a proteasome.

2. The method of claim 1, wherein said MHC class I pathway-associated component is a proteasome.

3. The method of claim 2, wherein said proteasome is a 20S or 26S proteasome.

4. The method of claim 1, wherein said inhibiting comprises introducing into said cell an antisense oligonucleotide that is complementary to all or a portion of an mRNA encoding said TAP protein, thereby inhibiting translation of said TAP protein.

5. The method of claim 1, wherein said TAP protein is TAP-1.

6. The method of claim 1, wherein said TAP protein comprises TAP-2.

7. The method of claim 1, wherein said cell is a T lymphocyte.

8. The method of claim 1, wherein said cell is an RMA cell.

9. The method of claim 1, wherein said cell is an adherent or non-adherent splenocyte.

10. The method of claim 1, wherein said cell is an adherent or non-adherent peripheral blood mononuclear cell.

11. The method of claim 1, wherein said cell is a dendritic cell.

12. The method of claim 1, wherein said cell is a macrophage.

13. The method of claim 1, wherein said cell is a cell of a thymoma.

14. The method of claim 4, wherein said antisense oligonucleotide is between 25 and 30 nucleotides in length and comprises the sequence

5'AGGGCCTCAGGTAGGACAGCGCCAT 3' (SEQ ID NO: 1).

15. The method of claim 4, wherein said antisense oligonucleotide is between 25 and 30 nucleotides in length and comprises the sequence

5'GCAGCAGGATATTGGCATTGAAAGG 3' (SEQ ID NO: 2).

16. The method of claim 1, wherein said cell is a B lymphocyte.

17. The method of claim 1, wherein said peptide is a tumor-specific antigen.

18. The method of claim 1, wherein said inhibiting comprises contacting said cell with a competitive proteasome inhibitor.

19. The method of claim 18, wherein said competitive proteasome inhibitor is CEP1601.

20. The method of claim 18, wherein said competitive proteasome inhibitor is selected from the group consisting of LlnL, MG115, MG132, CEP690, CEP1508, CEP1513, CEP1612, and lactacystin.

21. The method of claim 20, wherein said competitive proteasome inhibitor is MG132.

22. A mammalian cell produced by the method of claim 1.

23. A mammalian cell in vitro containing an antisense oligonucleotide that reduces expression of an MHC class I pathway-associated protein, wherein said MHC class I pathway-associated protein is a TAP protein.

24. A method for stimulating proliferation of a T lymphocyte in vitro, said method comprising contacting said T lymphocyte with the cell of claim 22.

25. A cytotoxic T lymphocyte produced by:

inhibiting activity of an MHC class I pathway-associated component in a mammalian cell in vitro, wherein said MHC class I pathway-associated component is a TAP protein or a proteosome;

contacting said cell with an antigen, thereby producing an antigen presenting cell; and contacting a T lymphocyte with said antigen presenting cell in vitro, thereby producing a cytotoxic T lymphocyte.

26. The lymphocyte of claim 25, wherein said MHC class I pathway-associated component is a TAP protein.

27. The lymphocyte of claim 25, wherein said MHC class I pathway-associated component is a proteasome.

* * * * *